US006525210B1

(12) United States Patent
Zhang et al.

(10) Patent No.: US 6,525,210 B1
(45) Date of Patent: Feb. 25, 2003

(54) CHIRAL LIGANDS, TRANSITION-METAL COMPLEXES THEREOF AND USES THEREOF IN ASYMMETRIC REACTIONS

(75) Inventors: Xumu Zhang, State College, PA (US); Dengming Xiao, Longmont, CO (US)

(73) Assignee: The Penn State Research Foundation, University Park, PA (US)

(*) Notice: Subject to any disclaimer, the term of this patent is extended or adjusted under 35 U.S.C. 154(b) by 0 days.

(21) Appl. No.: 09/643,434

(22) Filed: Aug. 22, 2000

Related U.S. Application Data

(60) Provisional application No. 60/150,375, filed on Aug. 23, 1999, and provisional application No. 60/165,649, filed on Nov. 15, 1999.

(51) Int. Cl.[7] ................................................. C07F 9/50
(52) U.S. Cl. .............................. 556/21; 568/12; 560/8; 562/425
(58) Field of Search ............................. 568/12; 556/21; 564/15; 560/8; 562/405

(56) References Cited

U.S. PATENT DOCUMENTS

| | | | |
|---|---|---|---|
| 5,202,493 A | 4/1993 | Burk | 568/12 |
| 5,329,015 A | 7/1994 | Burk | 549/10 |
| 5,648,547 A * | 7/1997 | Regnat | 568/12 |
| 6,037,500 A1 * | 3/2001 | Zhang | 568/12 |

OTHER PUBLICATIONS

CA:118:7054 abs of J Chem Soc Chem Commun by Alder et al (17) pp 1172–1174 1992.*
CA:124:276831 abs of Inorg Chem by Field et al 35(9) pp 2546–2548 1996.*
CA:124:289833 abs of Main Group chem by Kang et al 1(1) pp89–98 1995.*
Inorg Chem by Bitterer et al 37 pp 6408–6417 1998.*
Takaya et al. "BINAP: An Efficient Chiral Element for Asymmetric Catalysis," Acc. Chem. Res., 1990, 23, 345–350.
Bitterer et al., "PH–Functional Phosphines with 1,1'–Biphenyl–2,2'–bis (methylene and 1,1'–Binaphthyl–2,2'–bis(methylene) Backbones," Inorg. Chem., 1998, 37, 6408–6417.
Gladiali et al. "Novel Atropisomeric Phosphorus Ligands: 4,5–Dihydro–3H–dinaphtho[2,1–c;1',2'–e]phosphepine Derivatives," Tetrahedron: Asymmetry vol. 5, No. 4, 511–514, 1994.
Ohkuma et al., "Asymmetric Hydrogenation of Alkenyl, Cyclopropyl, and Aryl Ketones. RuCl2 (xylbinap) (1,2–diamine) as a Precatalyst Exhibiting A Wide Scope," J. Am. Chem. Soc., 1998, 120, 13529–13530.
Maigrot et al. "New and Improved Synthesis of Optically Pure ( R )—and (S)–2,2'–Dimethyl–1,1'–binaphthyl and Related Compounds," Groupe de Recherche n° 12, C.N.R.S., 2 rue H. Dunant, F–94320, Thiais, France, 317–320, Mar. 1985.

Reetz et al. "Diphosphonites as highly efficient ligands for enantioselective rhodium–catalyzed hydrogenation," Chem. Commun., 1998, 2077–2078.
Schnider et al., "Enantioselective Hydrogenation of Imines with Chiral (Phosphanodihydrooxazole)iridium Catalysts," Chem. Eur. J. 1997, 3, No. 6, 887–892.
Uozumi et al., "Synthesis of Optically Active 2–(Diarylphosphino)–1, 1'–binaphthyls, Efficient Chiral Monodentate Phosphine Ligands," J. Org. Chem., 1993, 58, 1945–1948.
Chong et al., "4,5–Dihydro–4,4–demethyl–3H–dinaphtho [2,1–c:1',2'–e]stannepin as a Precursor of 2,2'–Bis(lithiomethyl)–1,1'–binaphthyl," J. Org. Chem., 1993, 58, 1266–1268.
Sengupta et al. "Ni(0)–Catalyzed Cross Coupling of Aryl O–Carbamates and Aryl Triflates with Grignard Reagents. Directed Ortho Metalation–Aligned Synthetic Methods for Polysubstituted Aromatics via a 1,2–Dipole Equivalent," J. Org. Chem., 1992, 57, 4066–4068.
Cai et al., "Simple and Efficient Resolution of 1,1'–Bi–2–naphthol," Tetrahedron Letters, vol. 36, No. 44, 7991–7994, 1995.
Okamoto et al., "Synthesis and Herbicidal Activity of N–(1–Arylethenyl)–2–chloroacetamides," Agric. Biol. Chem., 55 (11), 2733–2736, 1991.
Burk et al., "A Convenient Asymmetric Synthesis of α–1–Arylalkylamines through the Enantioselective Hydrogenation of Enamides," J. Am. Chem. Soc. 1996, 118, 5142–5143.
Burk, "C2–Symmetric Bis(phospholanes)and Their Use in Highly Enantioselective Hydrogenation Reactions," J. Am. Chem. Soc. 1991, 113, 8518–8519.
Milart et al., "The Reaction of Arylidenemalonodinitriles with 1–Arylethylideneaminobenzenes. A New Synthesis of 5'–Amino–1,1':3',1"–terphenyl–2'–6'–dicarbonitriles, Dept. of Organic Chemistry, Jagiellonian Univ., Krakow, Poland, 41b, 371–376, 1986.
Burk et al., "Preparation and Use if C2–Symmetric Bis(phospholanes): Production of α–Amino Acid Derivatives via Highly Enantioselective Hydrogenation Reactions," J. Am. Chem. Soc., 1993, 115, 10125–10138.

* cited by examiner

*Primary Examiner*—Jean F. Vollano
(74) *Attorney, Agent, or Firm*—Ohlandt, Greeley, Ruggiero & Perle, L.L.P.

(57) ABSTRACT

Chiral ligands and transition metal complexes based on such chiral ligands useful in asymmetric catalysis are disclosed. The chiral ligands include phospholanes, P,N ligands, N,N ligands, biphenols, and chelating phosphines. The ferrocene-based irridium (R,R)-f-binaphane complex reduces imines to the corresponding amines with 95–99.6% enantioselectivity and reduces β-substituted-α-arylenamides with 95% enantioselectivity. The transition metal complexes of the chiral ligands are useful in asymmetric reactions such as asymmetric hydrogenation of imines, asymmetric hydride transfer reactions, hydrosilylation, hydroboration, hydrovinylation, hydroformylation, allylic alkylation, cyclopropanation, Diels-Alder reaction, Heck reaction, isomerization, Aldol reaction, Michael addition and epoxidation reactions.

21 Claims, No Drawings

CHIRAL LIGANDS, TRANSITION-METAL COMPLEXES THEREOF AND USES THEREOF IN ASYMMETRIC REACTIONS

This application claims priority from Provisional Applications Serial No. 60/150,375 filed on Aug. 23, 1999 and Ser. No. 60/165,649 filed on Nov. 15, 1999.

BACKGROUND OF THE INVENTION

1. Field of the Invention

The present invention relates to chiral ligands and transition metal complexes thereof that are useful in asymmetric reactions. More particularly, the present invention relates to chiral phospholanes, P,N ligands, N,N ligands, biphenols, and chelating phosphines and transition metal complexes thereof that are useful in asymmetric catalysis.

2. Description of the Prior Art

Discovery of new chiral ligands has been an essential element in the development of highly enantioselective transition metal-catalyzed reactions. New structural motifs play an important role in dictating enantioselectivities and reactivities of a reaction. With the growing demand of enantiomerically pure compounds in pharmaceutical and agrochemical industry, asymmetric catalysis has become increasingly more important because of its high efficiency.

For example, biaryl atropisomeric ligands have been explored as effective ligand scaffolds for many asymmetric transformations. One of the most frequently used chiral chelating phosphines is BINAP (Noyori, R.; Takaya, H. *Acc. Chem. Res.* 1990, 23, 345, Ohkuma, T.; Koizumi, M.; Doucet, H.; Pham, T.; Kozawa, M.; Murata, K.; Katayama, E.; Yokozawa, T.; Ikariya, T.; Noyori, R. *J. Am. Chem. Soc.* 1998, 120, 13529.).

Another family of excellent chiral phosphines is so called DuPhos (Burk, U.S. Pat. No. 5,329,015, U.S. Pat. Nos. 5,202,493, 5,329,015, Burk, M, J. *J. Am. Chem. Soc.* 1991, 113, 8518, Burk, M. J.; Feaster, J. E.; Nugent, W. A.; Harlow, R. L. *J. Am. Chem. Soc.* 1993, 115, 10125. Burk, M. J.; Wang, Y. M.; Lee, J. R. *J. Am. Chem. Soc.* 1996, 118, 5142), which has a rigid 1, 2-bis(phosphino)benzene backbone and electron-donating phospholane groups.

Gladiali et al. (Gladiali, S.; Dore, A.; Fabbri, D.; Lucchi, O. D.; Manassero, M. *Tetrahedron Asymmetry,* 1994, 511.) made monodentate chiral phospholanes bearing the 1, 1'-binaphthyl framework. However the method for their synthesis is not feasible to make the corresponding chelating chiral phospholanes. Stelzer et al. (Bitterer, F.; Herd, O.; Kuhnel, M.; Stelzer, O.; Weferling, N.; Sheldrick, W. S.; Hahu, J.; Nagel, S.; Rosch, N. *Inorg. Chem.* 1998, 37, 6408) only made racemic chelating phospholanes.

Reetz et al. prepared chelating chiral phosphinites using readily accessible binaphthanols as starting materials and demonstrated that they are excellent ligands for Rh-catalyzed asymmetric hydrogenation of dehydroaminoacids (Reetz, M. T.; Gosberg, A.; Goddard, R.; Kyung, S. *J. Chem. Soc., Chem. Commun.* 1998, 2077). John Brown made a chiral phosphine and pyridine ligand with a biaryl chirality. Several related chiral ligands are shown in the Figure below.

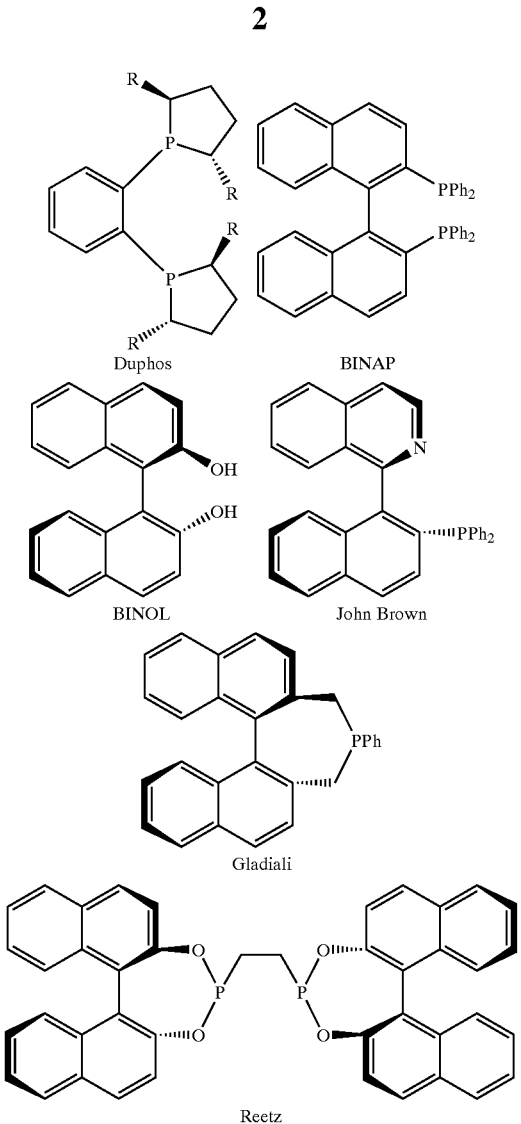

While these ligands have been useful in a number of asymmetric reactions, there are still many more asymmetric transformations that can benefit from the discovery of new chiral ligands.

SUMMARY OF INVENTION

The present invention includes a ligand selected from the group consisting of compounds represented by A through K:

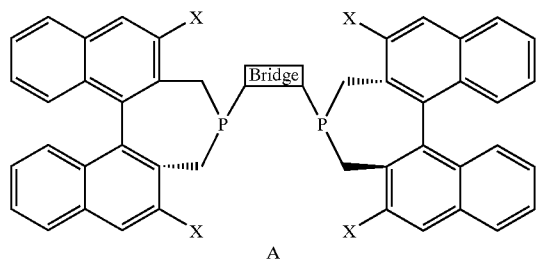

-continued

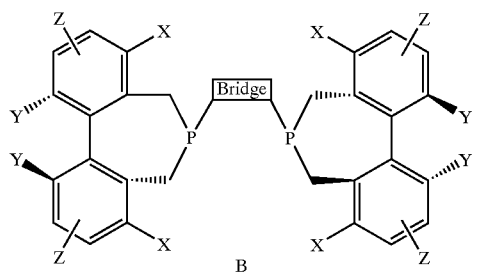

B

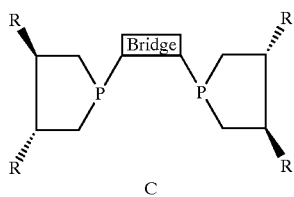

C

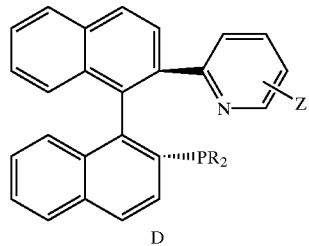

D

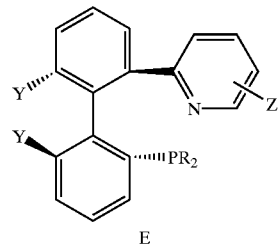

E

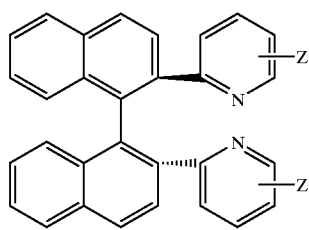

F

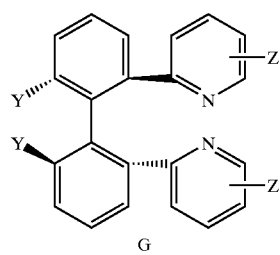

G

-continued

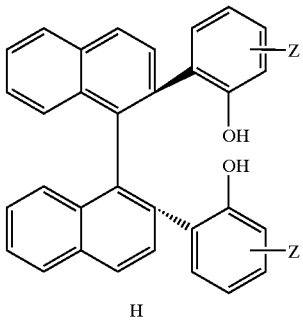

H

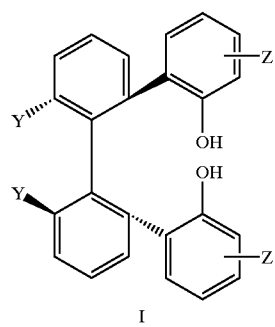

I

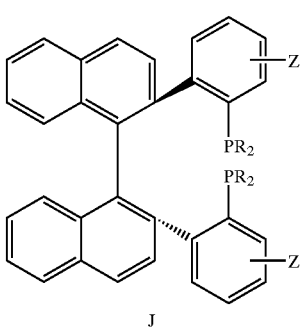

J

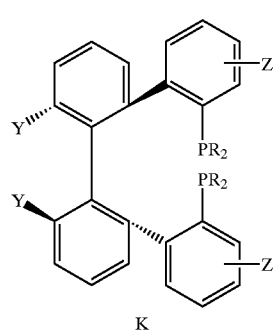

K herein the bridge group is selected from the group consisting of: $(CH_2)_n$ wherein n is an integer ranging from 1 to 8, $(CH_2)_nW(CH_2)_m$ wherein n and m are independently an integer ranging from 1 to 8 and W, wherein W is a divalent group selected from the group consisting of: 1,2-divalent phenyl, 2,2'-divalent 1,1'-biphenyl, 2,2'-divalent-1,1'-binaphthyl, ferrocene, and a substituted derivative thereof; wherein each substituent in said substituted derivative is selected from the group consisting of: aryl, alkyl having 1–8 carbon atoms, F, Cl, Br, I, COOR, SO₃R, PR₃R₂, OR, SR, PR₂, AsR₂, SbR₂, aryloxyl, nitro, NR₂, vinyl, substituted vinyl and a combination thereof, wherein each R is independently selected from the group consisting of: hydrogen, alkyl, aryl, alkaryl and aralkyl; wherein each X is independently selected from the group consisting of: hydrogen, halide, alkyl, aryl, alkoxy, silane, carboxylate and amide; each Y is independently selected from the group consisting of: hydrogen, alkyl, aryl, alkoxy, carboxylate and amide; and each Z is independently selected from the group consisting of: hydrogen, alkyl, aryl, alkoxy, amide, carboxylate, and a heterocyclic compound.

The present invention further includes a catalyst prepared by a process comprising contacting a transition metal salt, or a complex thereof, and a ligand selected from the group consisting of compounds represented by A through K as described above.

The present invention still further includes a process for preparation of an asymmetric compound using a catalyst according to the present invention. The process comprises contacting a substrate capable of forming an asymmetric product by an asymmetric reaction and a catalyst prepared by a process comprising contacting a transition metal salt, or a complex thereof, and a ligand selected from compounds represented by A through K as described above.

The ferrocene-based irridium (R,R)-f-binaphane complex reduces imines to the corresponding amines with 95–99.6% enantioselectivity and reduces β-substituted-α-arylenamides with 95% enantioselectivity.

DETAILED DESCRIPTION OF INVENTION

The present invention includes new phospholane ligands with mixed biaryl chirality. The P,N ligands, N,N ligands, biphenols and chelating phosphines are also derivatives of biaryl atropisomers. Also included are chiral five-membered ring phospholanes with stereogenic centers in 3,4 positions, phospholanes with a chiral biaryl atropisomer as the backbone and atropisomers of P,N ligands, N,N ligands, biphenols and chelating bisphophines. These chiral ligands can be used to facilitate a variety of metal-catalyzed asymmetric transformations. The bridge group can be $(CH_2)_n$ wherein n is an integer ranging from 1 to 8, $(CH_2)_nW(CH_2)_m$ wherein n and m are independently an integer ranging from 1 to 8 and W, wherein W is a divalent group selected from the group consisting of: 1,2-divalent phenyl, 2,2'-divalent 1,1'-biphenyl, 2,2'-divalent-1,1'-binaphthyl, ferrocene, and a substituted derivative thereof. Each substituent in the substituted derivative can be aryl, alkyl having 1–8 carbon atoms, F, Cl, Br, I, COOR, SO₃R, PR₃R₂, OR, SR, PR₂, AsR₂, SbR₂, aryloxyl, nitro, NR₂, vinyl, substituted vinyl and a combination thereof and each R can independently be hydrogen, alkyl, aryl, alkaryl and aralkyl. Each X can independently be hydrogen, halide, alkyl, aryl, alkoxy, silane, carboxylate and amide, each Y can independently be hydrogen, alkyl, aryl, alkoxy, carboxylate and amide and each Z can independently be hydrogen, alkyl, aryl, alkoxy, amide, carboxylate, and a heterocyclic compound (i.e., a nitrogen, sulfur or oxygen heterocycle).

For each class of A to K ligands, the corresponding enantiomer, as well as enantiomeric mixtures, are also contemplated. A and B ligands are chelating chiral phospholanes with biaryl chirality in their backbone. C ligands have five-membered ring phospholanes with stereogenic centers in 3,4 positions. D and E are chiral P,N ligands with biaryl chirality. F and G are chiral N,N ligands with biaryl chirality. H and I are chiral biphenols with biaryl chirality. J and K are chiral phosphines with biaryl chirality. The preferred ligands of the present invention are selected from ligands designated A through K, which include members represented by the formula L1 through L56 depicted below:

L1
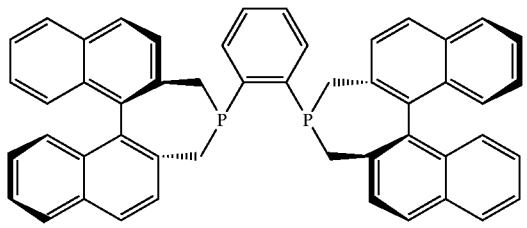

L2
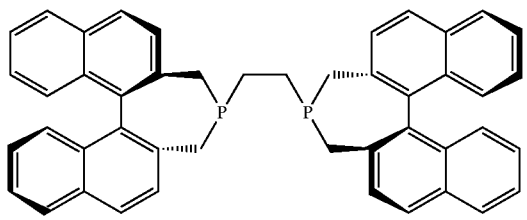

L3
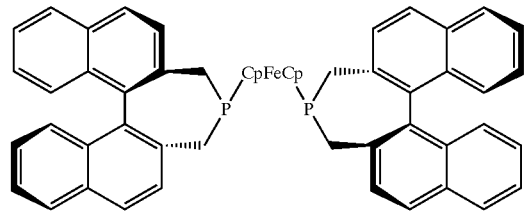

L4
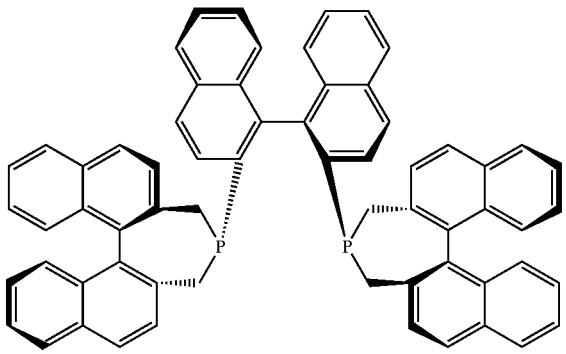

L5
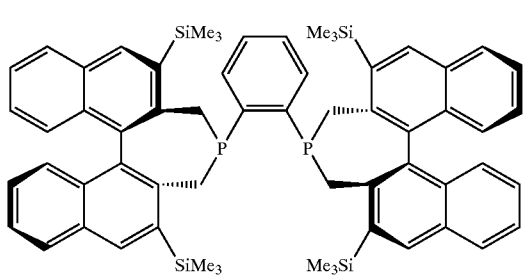

L6
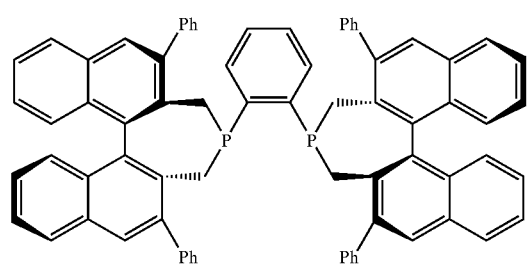
L7
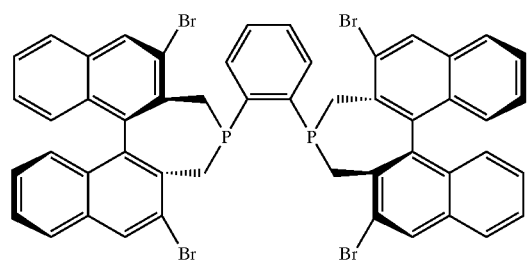
L8
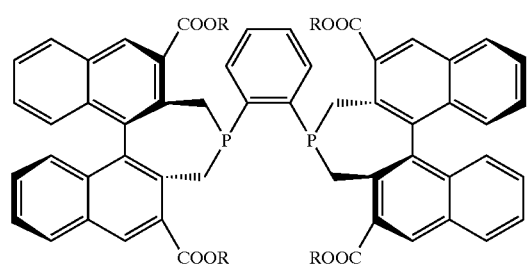
L9
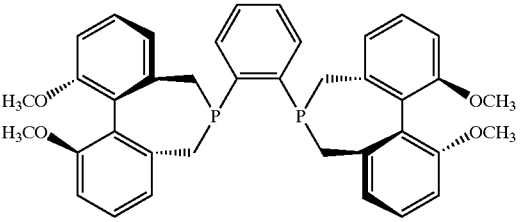
L10
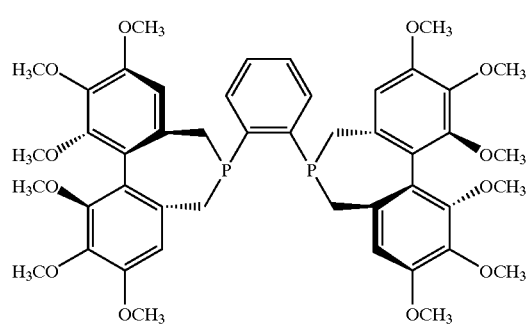
L11
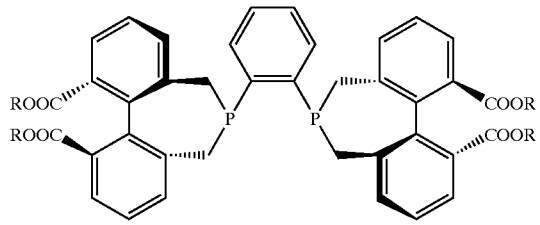
L12
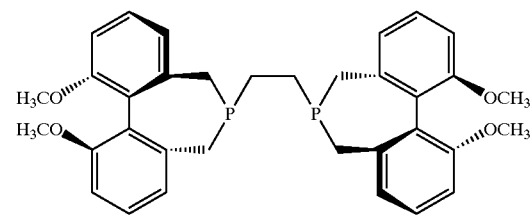
L13
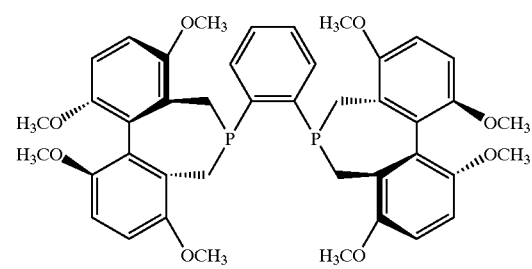
L14
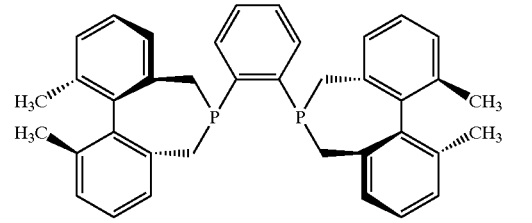
L15
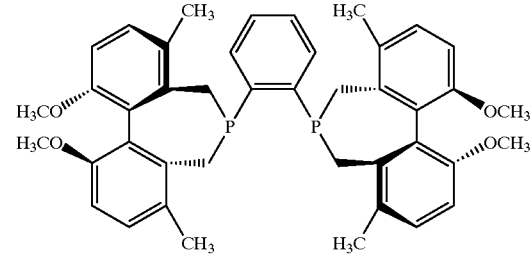
L16
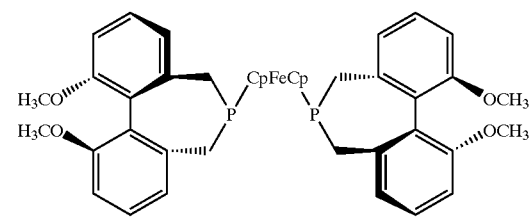

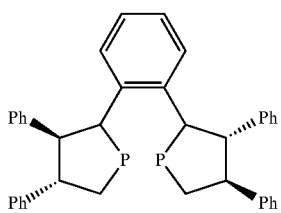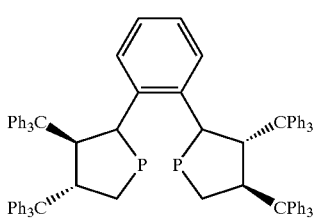

-continued

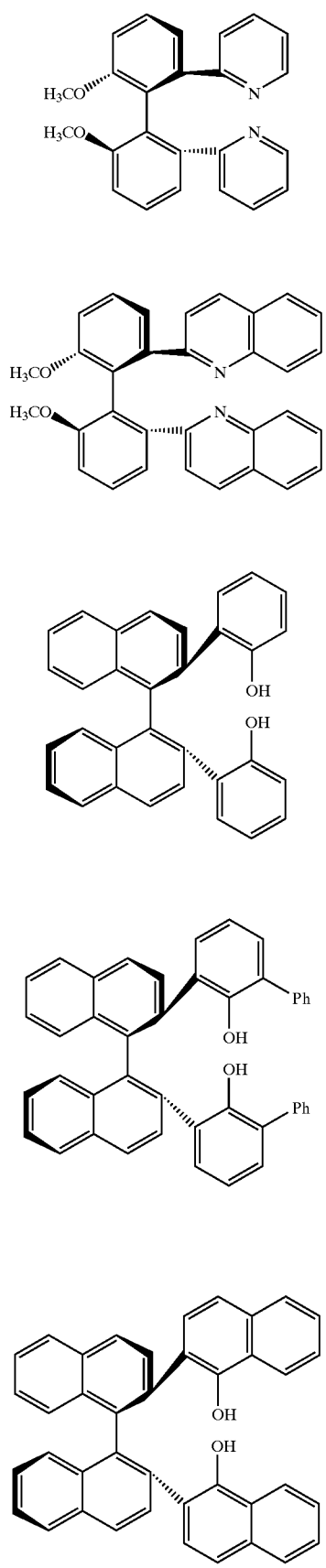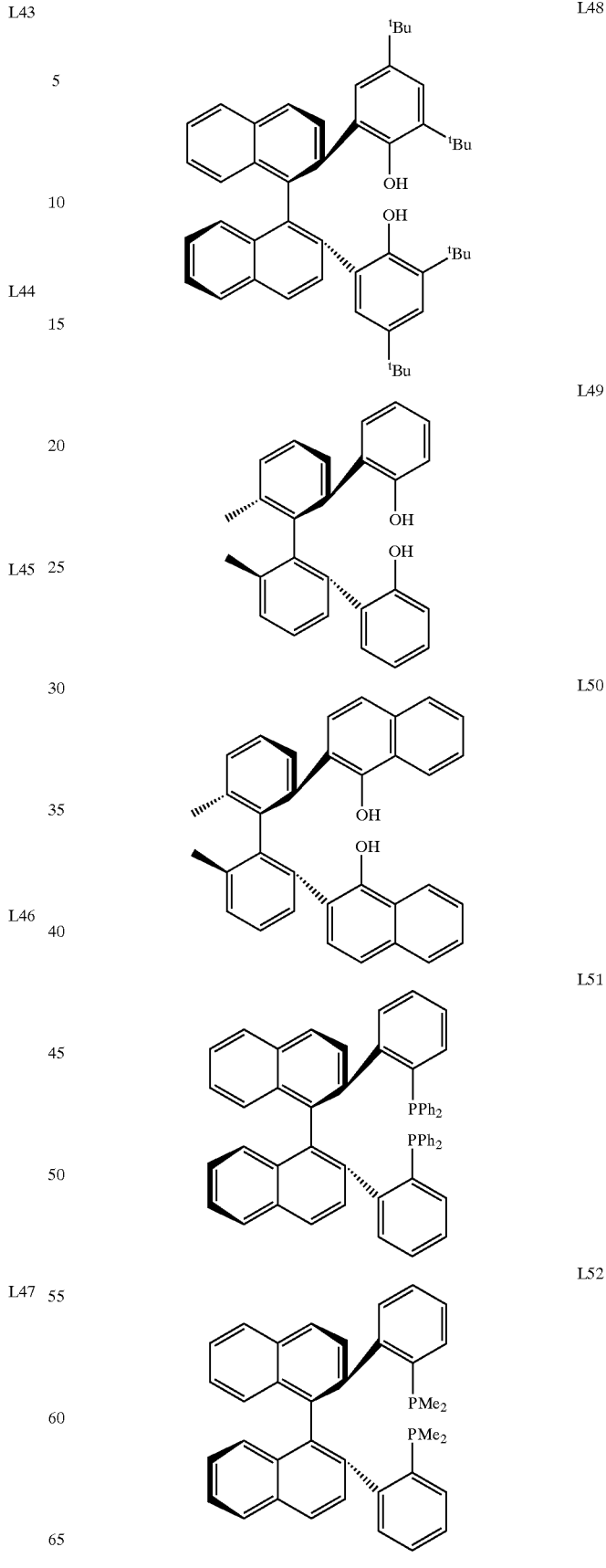

-continued

L53
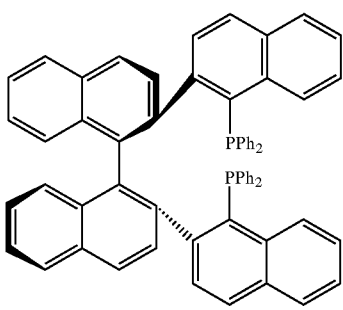

L54
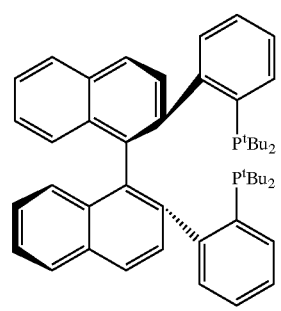

L55
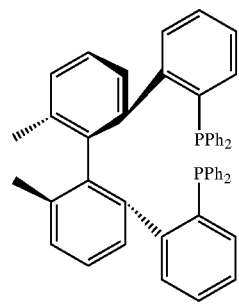

L56
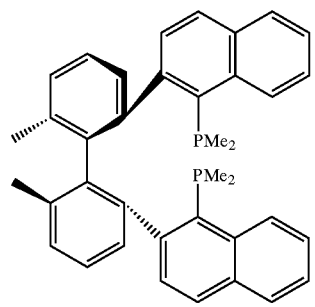

L1 to L8 are examples of A ligands. L9 to L16 are examples of B ligands. L17 to L24 are examples of C ligands. L25 to L35 are examples of D and E ligands. L36 to L44 are examples of F and G ligands. L45 to L50 are examples of F and G ligands. L51 to L56 are examples of J and K ligands.

f-Binaphane ligand and transition metal complexes thereof are preferred, irridium complexes of f-binaphane being the most preferred. The unsubstituted (R,R)-f-binaphane ligand is represented by the formula:

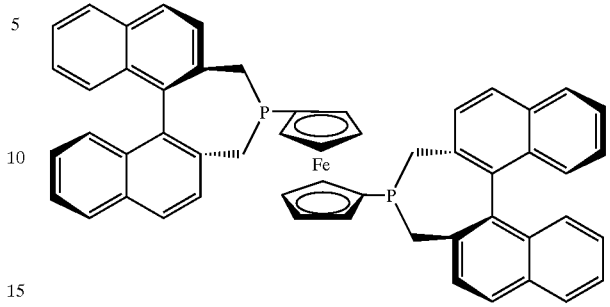

The highest enantioselectivity (>99%ee) has been achieved in the asymmetric hydrogenation of imines using Ir-f-binaphane complex as the catalyst.

The preparation of L1, L5, L17, L25, L36, L45, L51 and (R,R)-binaphane are illustrated below. Other members of L1 to L56 ligands can be prepared by similar procedures.

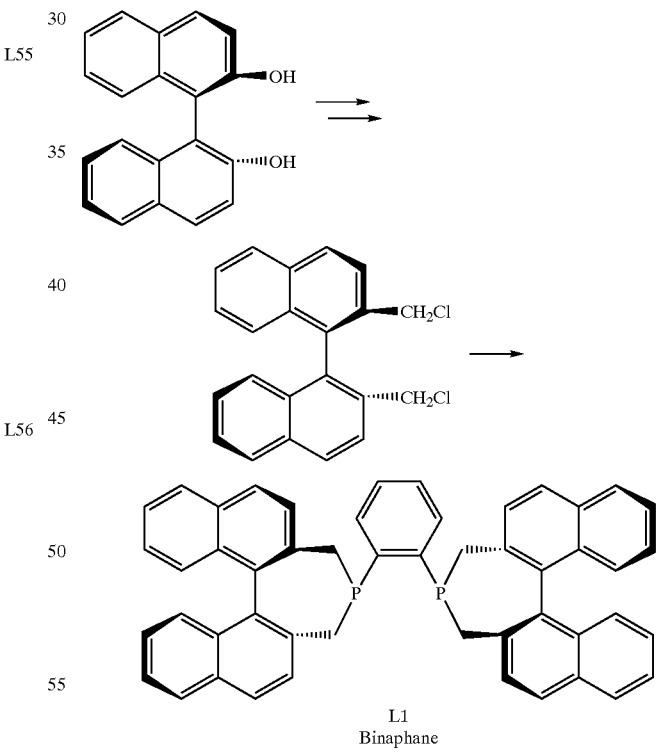

L1
Binaphane

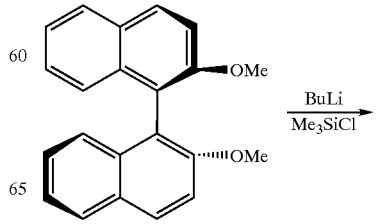

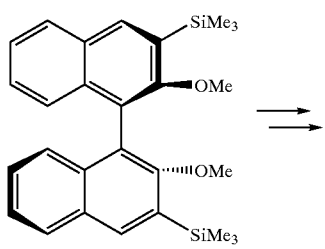
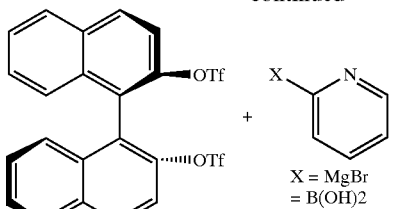
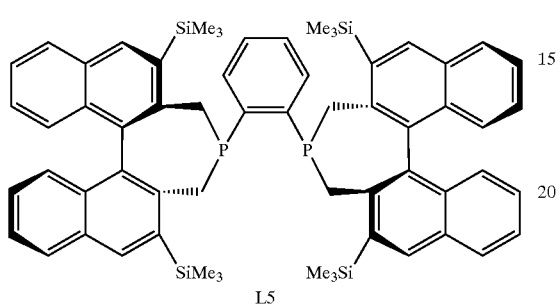
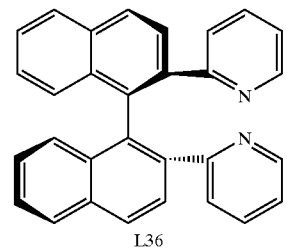
L36
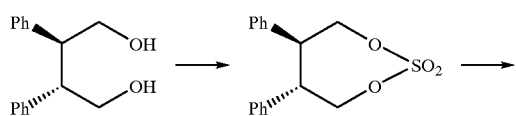
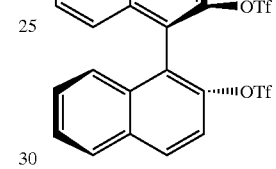
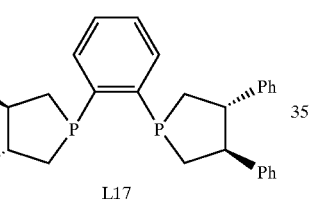
L17
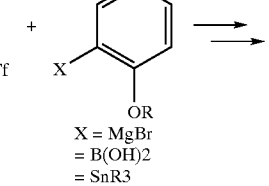
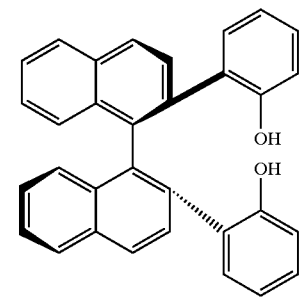
L45
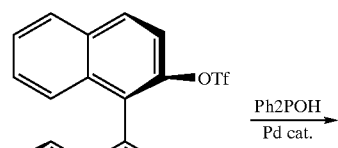
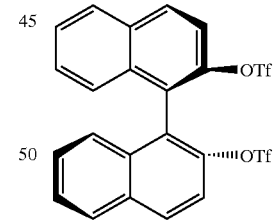
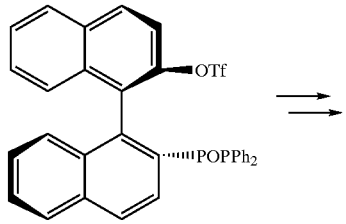
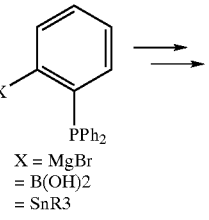
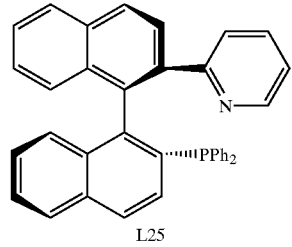
L25
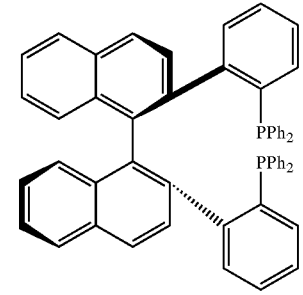
L51

The ligand according to the present invention can be racemic, i.e., racemic mixture of enantiomers, or a non-racemic mixture of enantiomers. Preferably, the ligand according to the present invention is one of the enantiomers. When the ligand is a non-racemic mixture of enantiomers, preferably it has an optical purity of at least 85%ee, more preferably, it has an optical purity of at least 95%ee.

According to the above reaction scheme, (R,R)-1,2-bis{(R)-4,5-dihydro-3H-dinaphtho[2,1-c:1',2'-e]phosphenino}benzene, abbreviated as (R,R)-binaphane, has been prepared in high yield and high optical purity. This chiral chelating phosphine has a rigid 1,2-bis(phosphino)benzene backbone and has both binaphthyl chirality and a phospholane functionality.

The preparation procedure is illustrated below:

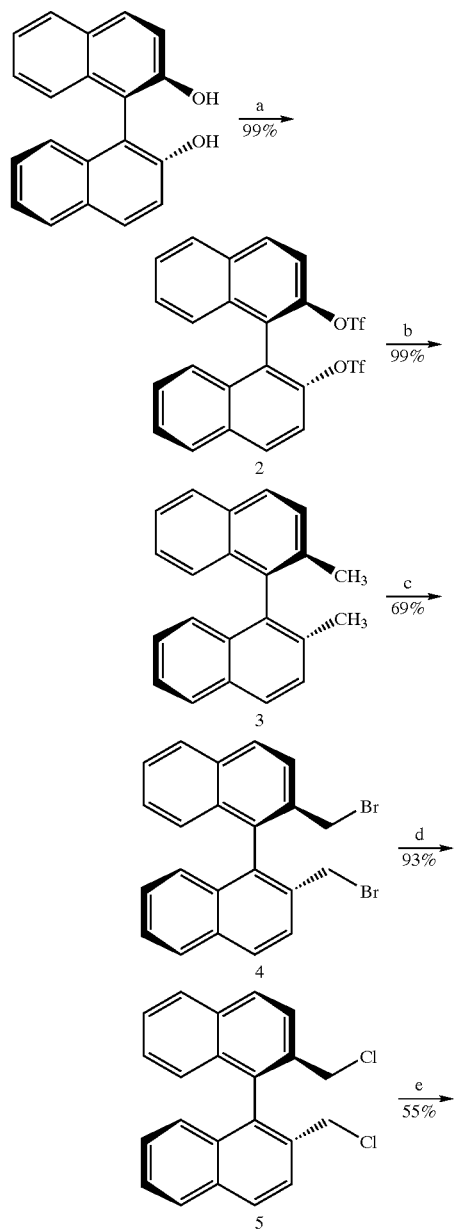

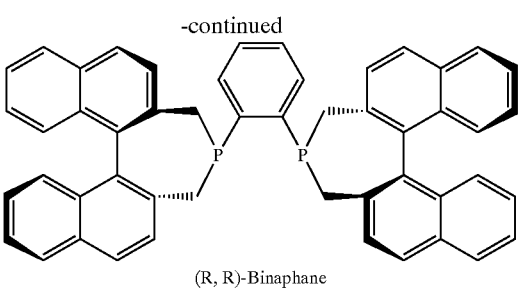

(R, R)-Binaphane

[a]Tf$_2$O, Py, CH$_2$Cl$_2$. [b]MeMgBr, NiCl$_2$(dppp), Et$_2$O. [c]NBS, Benzoyl peroxide, CCl$_4$. [d]LiCl, DMF. [e]1, 2-Bisphosphinobenzene, NaH, As illustrated schematically above, (R,R)-binaphane was prepared employing a practical synthesis route based on readily accessible starting materials. Enanatiomerically pure binaphthol can be easily obtained using a classic resolution procedure (Cai, D.; Hughes, D. L.; Verhoever, T. R.; Reider, P. J. *Tetrahedron Letter,* 1995, 7991). (R)-2,2'-bistriflate-1,1'-binaphthyl (2) was made from (R)-binaphthol by treating with excess triflic anhydride and pyridine in CH$_2$Cl$_2$. Kumada coupling of bistriflate (2) with methyl magnesium bromide gave (R)-2,2'dimethyl-1,1'-binaphthyl (3) in high yield. (R)-2,2'-Dibromomethyl-1,1'-binaphthyl (4) was prepared by bromination of 3 with NBS. A simple anion exchange of (R)-2,2'-dibromomethyl-1,1'-binaphthyl (4) with LiCl afforded (R)-2,2'-dichloromethyl-1,1'-binaphthyl (5) in high yield. A key element of our synthesis of chelating phospholane such as binaphane is utilization of a less reactive (R)-2,2'-dichloromethyl-1,1'-binaphthyl (5) to avoid the intermolecular reaction with phosphine anions which existed when using a more reactive (R)-2,2'-dibromomethyl-1,1'-binaphthyl (4). Refluxing (R)-2,2'-dichloromethyl-1,1'-binaphthyl (5) with 1,2-bis(phosphino)benzene and NaH in THF followed by recrystallization from ether gave (R,R)-binaphane in 55% yield. This efficient synthesis allows us to make binaphane in a large scale. Using this procedure, we have also made the corresponding monodentate chiral binaphthyl phospholane from phenylphosphine in >90% yield.

In a similar connectivity as in binaphane, new chiral five-membered ring chelating phospholanes with stereogenic centers in 3,4 positions can be effective. An important transformation in making the binaphthyl phospholane ligand is Kumada coupling of ArOTf with RMgBr (from 2 to 3). Stille and Suzuki coupling may also work as well. Based on these coupling strategies, a series of new atropisomers of P,N ligands, N,N ligands, biphenols and chelating bisphosphines can be derived.

Chiral f-binaphane (or a substituted derivative thereof) was prepared according to a process comprising contacting chiral 1,1'-di(chloromethyl)binaphthyl (or a substituted derivative thereof) and 1,1'-bisphosphinoferrocene (or a substituted derivative thereof) in the presence of a base and a solvent to produce f-binaphane (or the substituted derivative thereof). Preferably, the base is NaH and the solvent is tetrahydrofuran is (THF).

The present invention also includes a catalyst prepared by a process comprising contacting a transition metal salt, or a complex thereof, and a ligand selected from the group consisting of compounds represented by A through K.

As for the ligand, the catalyst according to the present invention can be racemic, such as, a racemic mixture of enantiomers, or it can be a non-racemic mixture of enantiomers. Preferably, the catalyst according to the present invention is one of the enantiomers. When the ligand according to the present invention is a non-racemic mixture of enantiomers, preferably it has an optical purity of at least 85%ee, more preferably, it has an optical purity of at least 95%ee.

Suitable transition metals for the preparation of the catalyst include Pt, Pd, Rh, Ru, Ir, Cu, Ni, Mo, Ti, V, Re and Mn.

The catalyst can be prepared by contacting a transition metal salt or its complex and a ligand selected from A through K. The transition metal salt or complex can be $PtCl_2$; $Pd_2(DBA)_3$; $Pd(OAc)_2$; $PdCl_2(RCN)_2$; $[Pd(allyl)Cl]_2$; $[Rh(COD)Cl]_2$; $[Rh(COD)_2]X$; $Rh(acac)(CO)_2$; $Rh(ethylene)_2(acac)$; $Rh(CO)_2Cl_2$; $Ru(RCOO)_2$(diphosphine); $Ru(methylallyl)2(diphosphine)$; $Ru(aryl group)X_2(diphosphine)$; $RuCl_2(COD)$; $[Rh(COD)_2]X$; $RuX_2(diphosphine)$; $RuCl_2(=CHR)(PR'_3)_2$; $Ru(ArH)Cl_2$; $Ru(COD)(methylallyl)_2$; $[Ir(COD)_2Cl]_2$; $[Ir(COD)_2]X$; $Cu(OTf)$; $Cu(OTf)_2$; $Cu(Ar)X$; $CuX$; $NiX_2$; $Ni(COD)_2$; $MoO_2(acac)_2$; $Ti(OiPr)_4$; $VO(acac)_2$; $MeReO_3$; $MnX_2$ or $Mn(acac)_2$; wherein each R and R' can independently be alkyl or aryl; Ar is an aryl group; and X is a counteranion. The preferred counteranions include halogen, $BF_4$, $ClO_4$, $SbF_6$, $CF_3SO_3$ and a mixture thereof.

The catalyst may be prepared in situ or as an isolated compound. An example of the preferred catalyst of the present invention is chiral Ir-f-binaphane catalyst.

In another aspect, the present invention includes a process for preparation of an asymmetric compounds using the catalysts described above. The process includes the step of contacting a substrate capable of forming an asymmetric product by an asymmetric reaction and a catalyst prepared by contacting a transition metal salt, or a complex thereof, and a ligand selected from ligands represented by A through K.

Suitable asymmetric reactions is include hydrogenation, hydride transfer, hydrosilylation, hydroboration, hydrovinylation, hydroformylation, allylic alkylation, cyclopropanation, Diels-Alder reaction, Heck reaction, isomerization, Aldol reaction, Michael addition and epoxidation. Preferably, the asymmetric reaction is hydrogenation and the substrate to be hydrogenated is an ethylenically unsaturated compound, imine, ketone, enamine, enamide, and vinyl ester. Suitable catalysts for the hydrogenation of imines to produce a chiral amine include Ir complex of chiral f-binaphane and Rh complex of chiral binaphane.

To test synthetic utility of (R,R)-binaphane, asymmetric hydrogenation of enamides using a Rh-(R,R)-binaphane complex as the catalyst was conducted. The imine reduction may be carried out in the presence of additional catalysts, such as iodine or $H^+$.

Initially, several experiments were performed to screen optimal conditions for hydrogenation of N-acetyl-phenylethenamine. $Rh(COD)_2PF_6$ was found as a better catalyst precursor compared with a neutral Rh species $[Rh(COD)Cl]_2$. Increase of $H_2$ pressure results in decrease of enantioselectivity of the asymmetric hydrogenation. For example, 85%ee was obtained under 300 psi $H_2$ while 90%ee was achieved under 20 psi $H_2$. Variation of solvents causes dramatic changes in both enantioselectivity and reactivity. While hydrogenation was complete in $CH_2Cl_2$ with 90%ee, both reactivity and enantioselectivity were lower in methanol (14%ee and 86% conversion).

Several enamides were prepared according to literature procedures and were used as substrates for the asymmetric hydrogenation reaction. Table 1 lists results obtained under the optimal conditions for hydrogenation of N-acetyl-phenylethenamine (6a). Although very good enantioselec- tivity has been obtained for hydrogenation of α-arylenamides without substitituents in the β-position, the highlight of the Rh-binaphane catalyst is its ability to reduce β-substituted-α-arylenamides with excellent enantioselectivities. Several β-substituted-α-arylenamides with the mixture of (E)/(Z) isomers were reduced in high enantioselectivities (entries 7–13, 95%–99.6%ee). A small electronic effect was observed. These enantioselectivities with the Rh-(R,R)-binaphane catalyst is the highest reported to date. Since the product 7 can be easily converted to the corresponding arylalkylamine through hydrolysis under acidic condition, hydrogenation with the Rh-binaphane complex provides a practical method for preparing a variety of chiral arylalkylamines.

EXAMPLES

General Procedures

All reactions and manipulations were performed in a nitrogen-filled glove box or using standard Schlenk techniques. THF and toluene were dried and distilled from sodium-benzophenone ketyl under nitrogen. Methylene chloride was distilled from $CaH_2$. Methanol was distilled from Mg under nitrogen. (R,R)-BDNPB was made a solution of 10 mg/ml in toluene before use. Column chromatography was performed using EM silica gel 60 (230–400 mesh). $^1H$, $^{13}C$ and $^{31}P$ NMR were recorded on Bruker WP-200, AM-300, and AMX-360 spectrometers. Chemical shifts were reported in ppm down field from tetramethylsilane with the solvent resonance as the internal standard. Optical rotation was obtained on a Perkin-Elmer 241 polarimeter. MS spectra were recorded on a KRATOS mass spectrometer MS 9/50 for LR-EI and HR-EI. GC analysis was carried on Helwett-Packard 6890 gas chromatography using chiral capillary columns. HPLC analysis was carried on Waters™ 600 chromatography. Imines were prepared according to a reported procedure.

Synthesis of 1,2-Bis{(R)-4,5-dihydro-3H-dinaphtho[1,2-c;2',1'-e]phosphepino}benzene (R)-2,2'-bistriflate-1,1'-binaphthyl (2)

To a solution of (R)-BINOL (40.3 g, 140.7 mmol) in 900 mL of $CH_2Cl_2$ was added pyridine (40 mL) and followed by dropwise addition of triflic anhydride (50.5 mL, 300 mmol) at 0° C. The mixture was stirred at room temperature for 6 h. After removal of the solvent, the residue was diluted with EtOAc (500 mL) and then washed with 5% aqueous HCl (100 mL), saturated $NaHCO_3$ (100 mL) and brine (100 mL). The organic layer was dried over anhydrous sodium sulfate, concentrated and passed through a silica gel plug (eluted with $CH_2Cl_2$) to give the (R)-bistriflate (2) (77 g, 99%).

(R)-2,2'-dimethyl-1,1'-binaphthyl (3)

To a solution of (R)-bistriflate (2) (77 g, 140 mmol) and $NiCl_2.dppp$ (3.8 g, 7 mmol) in ether (1000 mL) was added dropwise the methyl magnusium bromide (3.0 M, 280 mL) at 0° C. The reaction mixture was heated to refluxing for 24 h. The reaction was quenched by addition of water (200 mL) slowly at 0° C. and then diluted with 5% aqueous HCl (200 mL). The aqueous layer was extracted with ether (3×100 mL). The combined organic layer was washed with $NaHCO_3$(100 mL), dried over anhydrous sodium sulfate and concentrated to afford 3 as light yellow color solid (39.2 g, 99%).

(R)-2,2'-dibromomethyl-1,1'-binaphthyl (4)

A mixture of (R)-2,2'-dimethyl-1,1'-binaphthyl (3) (39.2 g, 138.8 mmol), N-bromosuccinimide (52.4 g, 291.5 mmol) and benzoylperoxide (0.5 g) in tetrachlorocarbon (900 mL) was heated at refluxing and irradiated under a sunlight for three days. The mixture was cooled to room temperature and filtered. The filtrate was concentrated and passed through a silica gel plug. After removal of the solvent, the residue was recrystalized from $CH_2Cl_2$/hexanes to afford 2,2'-dibromomethyl-1,1'-dinaphthyl (4) (41.1 g, 67.3%).

(R)-2,2'-dichloromethyl-1,1'-binaphthyl (5)

(R)-2,2'-Dibromomethyl-1,1'-binaphthyl (4, 40 g, 90.8 mmol) and LiCl (30 g, 707 mmol) in DMF (800 mL) was mixed together and stirred at room temperature for 6 h. To this mixture was added carefully 5% aqueous HCl (300 mL) (exothermomic reaction occurred). The mixture was then extracted with ether (4×400 mL). The organic layer was dried over sodium sulfate, concentrated and recrystallized from $CH_2Cl_2$/hexane to gave 5 as white solid (30 g, 93%).

(R,R)-1,2-bis{(R)-4,5-dihydro-3H-dinaphtho[1,2-c;2',1'-e]phosphepino}benzene To a solution of (R)-2,2'-dichloromethyl-1,1'-binaphthyl (5, 0.57 g, 1.62 mmol) and NaH (0.2 g, 8.3 mmol) in THF (20 ml) was added 1,2-bis(phosphino)benzene (109 μl, 0.812 mmol) at −78° C. under nitrogen. The mixture was kept stirring at room temperature for 24 h and was heated at refluxing for 24 h. After the reaction was completed (monitored by $^{31}$P NMR), the solvent was removed via vacuum and the residue was washed with ether (3×15 mL). The organic phase was filtered through a silica gel plug to give the fairly pure product. Further purification by recrystallization from ether afforded binaphane (0.31 g, 55%). $^1$H NMR (CDCl$_3$) 360 MHz 7.83–7.8 (4H,m,Ar—H), 7.59–7.56 (2H,m,Ar—H), 7.33–7.15 (16H,m,Ar—H), 7.0–6.9 (2H,m,Ar—H), 6.8–6.7 (2H,m,Ar—H), 6.66–6.63 (2H,d,J=8.3 Hz,Ar—H), 2.97–2.74 (8H, m, ArCH$_2$); $^{31}$P NMR(CDCl$_3$) -5.63 ppm.

General Procedure for Catalytic Asymmetric Hydrogenation of Enamides

In a glove box, the Rh-phosphine complex was made in situ by mixing Rh(COD)$_2$PF$_6$ (3.7 mg, 0.008 mmol) and binaphane (0.8 mL of 10 mg/mL ligand in toluene, 0.012 mmol) in 19.2 mL of CH$_2$Cl$_2$. The mixture was stirred for 30 min. Then 2.5 mL of this solution was transferred to a 10 mL vial with an enamide substrate (0.1 mmol). Hydrogenation was performed at room temperature under 20 psi of hydrogen pressure for 24 h. The hydrogen was released carefully and the reaction mixture was passed through a silica gel plug eluted with EtOAc. The enantiomeric excess was measured by GC or HPLC using a chiral GC or HPLC column without further purification. The absolute configuration of products was determined by comparing the sign of optical rotation with the reported data (Table 1).

TABLE 1

Highly Enantioselective Hydrogenation of Enamides Catalyzed by Rh-(R,R)-Binapthane Complex[a]

| Entry | Substrate[c] | Ar | R | ee%[d] |
|---|---|---|---|---|
| 1 | 6a | $C_6H_5$ | H | 90.0 |
| 2 | 6b | 3-Me—$C_6H_4$ | H | 89.0 |
| 3 | 6c | 4-CF$_3$—$C_6H_4$ | H | 82.0 |
| 4 | 6d | 4-Ph—$C_6H_4$ | H | 75.7 |
| 5 | 6e | 4-Cy—$C_6H_4$ | H | 90.0 |
| 6 | 6f | 2-Np | H | 89.5 |
| 7 | 6g | $C_6H_5$ | $CH_3$ | 99.1 |
| 8 | 6h | 4-MeO—$C_6H_4$ | $CH_3$ | 99.6 |
| 9 | 6i | 4-CF$_3$—$C_6H_4$ | $CH_3$ | 97.0 |
| 10 | 6j | $C_6H_5$ | $CH_2CH_3$ | 97.0 |
| 11 | 6k | $C_6H_5$ | $CH_2Ph$ | 95.0 |
| 12 | 6l | $C_6H_5$ | $CH(CH_3)_2$ | 97.6 |
| 13 | 6m | 2-Np | $CH_3$ | 98.3 |

[a]The reaction was carried out at rt under an initial hydrogen pressure of 20 psi for 24 h. The catalyst w made in situ by stirring a solution of Rh(COD)$_2$PF$_6$ and (R,R)-Binaphane in CH$_2$Cl$_2$. [Substrate(0.04M)]:[Rh]:(R,R)-Binaphane = 100:1:1.5. The reaction went in quantitative yield.
[b]The configuration of product was determined by comparison of optical rotation with reported data.
[c]Enamides 6 were made according to the literature methods.
[d]Enantiomeric excesses were determined by chiral GC with a supelco chiral select 1000 column or by Chiral HPLC with a Regis (S,S)-Whelk-o1 column.

Highly enantioselective reduction of C-N double bond has drawn much attention in last few decades. Catalytic asymmetric hydrogenation of acyclic imines has remained among the toughest problems in synthetic chemistry despite several systems being effective in asymmetric hydrogenation of cyclic imines.

Recently Pfaltz et al. has reported that up to 89%ee can be achieved in enantioselective hydrogenation of N-phenyl imine of acetophenone with an Ir-P-N ligand complex as the catalyst. Enantioselectivities exceeding 90%ee in asymmetric hydrogenation of acyclic imines have rarely been reported in the literature.

According to the present invention, a high enantioselectivity (>99%ee) has been achieved in the synthesis of new chiral ligand (f-binaphane) and in the asymmetric hydrogenation using Ir-f-binaphane complex as the catalyst.

Synthesis of Chiral Phosphines (f-Binaphane)

This ligand was made via a route similar to that used to make binaphane. The 1,1'-diphosphinoferrocene was employed as the backbone to afford the new ligand more electron donating property that might be beneficial in transition metal catalyzed asymmetric reactions.

Synthesis of Chiral Phosphine f-Binaphane

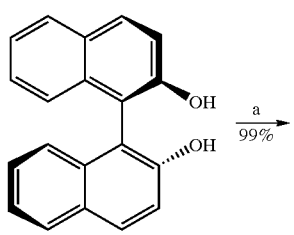

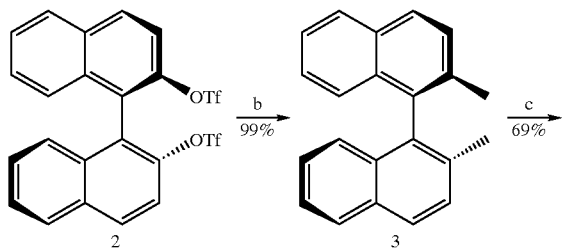

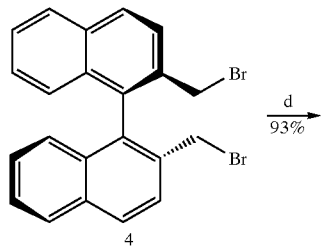

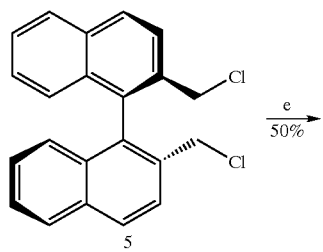

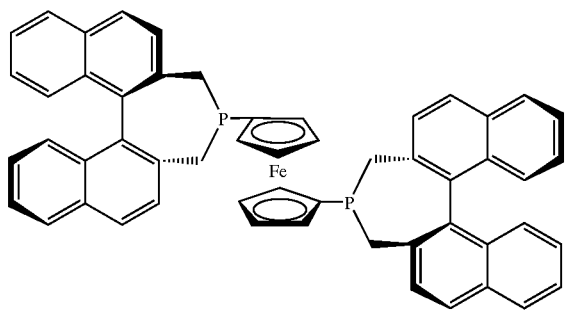

(R, R)-f-Binaphane

[a]Tf$_2$O, Py, CH$_2$Cl$_2$. [b]MeMgBr, NiCl$_2$(dppp), Et$_2$O. [c]NBS, Benzoyl peroxide, CCl$_4$. [d]LiCl, DMF. [e]1, 1'-Diphosphinoferrecene, NaH, THF.

(R,R)-1,1'-bis{(R)-4,5-dihydro-3H-dinaphtho[1,2-c:2',1'-e]phosphepino}ferrocene

To a solution of (R)-2,2'-dichloromethyl-1,1'-binaphthyl (5, 3.71 g, 10.56 mmol, prepared from (R)-BINOL via (R)-2,2'-bistriflate-1,1'-binaphthyl (2)[1], (R)-2,2'-dimethyl-1,1'-binaphthyl (3)[2], (R)-2,2'-dibromomethyl-1,1'-binaphthyl (4)[3], (R)-2,2'-dichloromethyl-1,1'-binaphthyl (5)[4] as previously described above) and NaH (2.0 g, 83.0 mmol) in THF (125 ml) was added 1,1'-di(phosphino)ferrocene (1.32 g, 5.28 mmol) at −78° C. under nitrogen. The mixture was kept stirring at room temperature for 24 h and was heated at refluxing for 24 h. After the reaction was completed (monitored by $^{31}$P NMR), the solvent was removed via vacuum and the residue was washed with CH$_2$Cl$_2$ (3×25 mL). The organic phase was filtered through a silica gel plug to give the fairly pure product. Further purification by recrystallization from Hexanes afforded (R,R)-1,1'-bis{(R)-4,5-dihydro-3H-dinaphtho[1,2-c:2',1'-e]phosphepino}ferrocene (2.15 g, 50%). $^1$H NMR (CDCl$_3$) 360 MHz δ7.81–7.76 (8H, m, Ar—H), 7.57–7.54 (4H, m, Ar—H), 7.31–7.13 (10H, m, Ar—H), 7.00–6.90 (2H, m, Ar—H), 6.80–6.70 (2H, m, Ar—H), 6.64–6.62 (2H,d, J=8.34 Hz, Ar—H), 2.97–2.74 (8H, m, ArCH$_2$); $^{13}$C NMR (CDCl$_3$) δ141.70, 134.71, 134.21, 133.40, 133.27, 132.73, 132.54, 132.34, 131.20, 128.83, 128.69, 128.62, 128.08, 127.80, 127.13, 127.10, 126.32, 125.46, 125.26, 32.50, 29.83; $^{31}$P NMR(CDCl$_3$) δ−6.87. MS m/z: 698 (M$^+$) (References: (1) Uozumi, Y.; Tanahashi, A.; Lee, S-Y.; Hayashi, T. *J. Org. Chem.* 1993, 58, 1945; (2) Sengupta, S.; Leite, M.; Raslan, D. S.; Quesnelle, C.; Snieckus, V. *J. Org. Chem.* 1992, 57, 4066; (3) Maigrot, N.; Mazaleyrat, J-P. *Synthesis*, 1985, 317; and (4) Chong, J. M.; MacDonald, G. K.; Park, S. B.; Wilkinson, S. H. *J. Org. Chem.* 1993, 58, 1266).

Enantioselective Hydrogenation of Imines

The N-phenyl imine of acetophenone was used to screen the reacion condition. Finally, the optimized condition was set as described below.

Enantioselective Hydrogenation of Acyclic Imines
Catalyzed by Ir-f-Binaphane

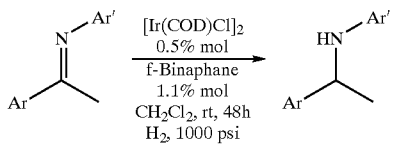

| Conversion | 100% | 100% | 80.3% | 77.2% |
|---|---|---|---|---|
| ee | 84.5% | >99% | 98.8% | 97.8% |

Other substrates were tried and we found that the bigger N-aryl group plays a very important role for high enantioselectivities. Changing the aryl group of aryl-alkyl ketone has no obvious effect on enantioselectivity.

General Procedure for Catalytic Asymmetric Hydrogenation of Imines

In a glove box, the Ir-phosphine complex was made in situ by mixing [Ir(COD)Cl]$_2$ (6.7 mg, 0.01 mmol) and the phosphine complex (0.022 mmol) in 20 mL of CH$_2$Cl$_2$ and stirring for 30 min. Then 5 mL of the solution was transferred to a 10 mL vial with an imine substrate (0.5 mmol). The hydrogenation was performed at rt under 1000 psi of hydrogen pressure for 48 h. The hydrogen was released carefully and the reaction mixture was passed through a silica gel plug eluted with EtOAc. The enantiomeric excess was measured by using GC with a chiral GC column without further purification.

In addition to the chiral ligand binaphane, which has been prepared from chiral BINOL and has shown excellent performance in Rh-catalyzed asymmetric hydrogenation of enamides, the present invention further includes a new chiral chelating phosphine, f-binaphane, which similarly bears binaphthyl moieties but is connected by a 1,1'-bisphosphinoferrocene backbone.

The new ligand, f-binaphane, was synthesized by a route similar to the preparation binaphane. Chiral binol was transformed into bistriflates 2, followed by dimethylation through Kumada coupling, bromination with NBS and anion exchanging with LiCl, afforded 1,1'-di(chloromethyl) binaphthyl 5. Refluxing dicholoride 5 with 1,1'-bisphosphinoferrocene in the presence of NaH in THF, followed by recrystallization from CH$_2$Cl$_2$/Hexanes, gave the pure f-binaphane product as a yellow solid.

In addition to the simple synthetic route, the stability of the f-binaphane ligand in the air as well as in solvent (at least for two days) makes the new ligand more attractive.

One of the important features of f-binaphane is its electron-rich property due to the two methylene groups and the ferrocene backbone binding to the phosphorus atom. This feature may be responsible for higher asymmetric induction for hydrogenation of unsaturated compounds. Another important feature is the flexibility of the ferrocene backbone that enables the f-binaphane ligand to chelate different transition metals as easily as BINAP does.

Furthermore, the coordination of the transition metal with chiral ligand will fix the configuration of the complex and provide a prominent chiral environment in which two binaphthyl groups occupy exactly two opposite quadrants, leaving the other two quadrants vacant. As a result, the ferrocene backbone makes the chiral pocket even broader and deeper and thus accessible to many bulky substrates.

The new ligand was applied to the so far unsolved imine reduction problem. In contrast to many catalytic enantioselective hydrogenation of olefins and ketones, only very limited success has been achieved by others in asymmetric hydrogenation of imines. The first attempt of f-Bianphane in hydrogenation of N-(1-phenylethylidene)aniline produced 84%ee at room temperature with 1% Ir-catalyst loading. The optimal condition was screened using the same substrate as the model substrate. The results are summarized in Table 2 below.

TABLE 2

Enantioselective Hydrogenation of N-(1-Phenylethylidene)aniline Catalyzed by Ir-f-Binaphane Complex[a]

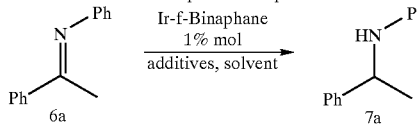

| entry | additive | solvent | T/° C. | $P_{H_2}$/psi | t/h | conversion % | ee%[b] |
|---|---|---|---|---|---|---|---|
| 1 | — | $CH_2Cl_2$ | rt | 1000 | 40 | 100 | 84.0 |
| 2 | — | THF | rt | 1000 | 40 | 97.2 | 83.3 |
| 3 | — | Toluene | rt | 1000 | 40 | 75.8 | 23.4 |
| 4 | — | MeOH | rt | 1000 | 40 | 71.2 | 64.0 |
| 5 | — | $CH_2Cl_2$ | rt | 400 | 48 | 97.8 | 84.0 |
| 6 | — | $CH_2Cl_2$ | −5 | 1000 | 64 | 94.5 | 84.0 |
| 7 | Phthalimide 4% | $CH_2Cl_2$ | rt | 1000 | 24 | 100 | 82.7 |
| 8 | $^nBu_4NI$ 4% | $CH_2Cl_2$ | rt | 1000 | 24 | 100 | 72.9 |
| 9 | $PhCH_2NH_2$ 4% | $CH_2Cl_2$ | rt | 1000 | 24 | 8.8 | 62.0 |
| 10 | AcOH 35eq | $CH_2Cl_2$ | rt | 1000 | 24 | 48 | 71.8 |

[a]The reaction was carried out in autoclave by mixing the substrate with catalyst in solvent and pressurized with hydrogen. The catalyst was made in situ by stirring a solution of $[Ir(COD)Cl]_2$ and (R,R) f-Binaphane in solvent. [Substrate (0.1M)]:[Ir]:(R,R) f-Binaphane = 100:1:1.1.
[b]Enantiomeric excess was determined by chiral GC with a Supelco chiral select 1000 column. Absolute configurations was not determined.

Neutral precursor $[Ir(COD)Cl]_2$ has better performance than cationic $Ir(COD)_2PF_6$. The weakly coordinating solvent $CH_2Cl_2$ is preferred over other solvent such as THF, toluene or MeOH (entries 1–4). Decreasing the hydrogen pressure has no obvious improvement on enantioselectivity but drops the reactivity (entry 5). The temperature effect is negligible (entry 6). The additive effect that shows a great improvement on enantioselectivity in many systems was not found in this case (entries 7–10). However, phthalimide and tetrabutylammonium iodide did accelerate the reaction to a small extent (entries 7–8).

When 2,6-dimethylphenyl group was employed to replace N-phenyl group, surprisingly >99% enantioselectivity was achieved. To our knowledge, this is the highest enantioselectivity achieved so far for asymmetric hydrogenation of acyclic imines.

These results are summarized in Table 3.

TABLE 3

Enantioselective Hydrogenation of Acyclic Imines Catalyzed by Ir-f-Binaphane Complex[a]

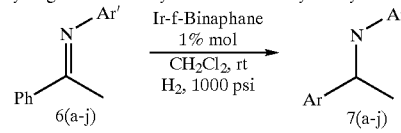

| entry | substrate | Ar | Ar' | t/h | conversion % | ee %[b] |
|---|---|---|---|---|---|---|
| 1 | 6a | Ph | Ph | 40 | 100 | 84.0 |
| 2 | 6b | Ph | 2,6-dimethyl-$C_6H_3$ | 44 | 76.8 | >99 |
| 3 | 6c | 4-MeO—$C_6H_4$ | 2,6-dimethyl-$C_6H_3$ | 44 | 77.2 | 97.8 |
| 4 | 6d | 4-$CF_3$—$C_6H_4$ | 2,6-dimethyl-$C_6H_3$ | 44 | 80.3 | 98.8 |
| 5 | 6e | N-(2,3,4-trihydro-1-naphthylidene) | 2,6-dimethylaniline | 44 | 23.8 | 96.8 |
| 6 | 6f | t-Bu | 2,6-dimethyl-$C_6H_3$ | 44 | 14.9 | 8.3 |
| 7 | 6g | $^iPr$ | 2,6-dimethyl-$C_6H_3$ | 44 | 28.8 | 22.6 |
| 8 | 6h | Cy | 2,6-dimethyl-$C_6H_3$ | 44 | 24.2 | 31.4 |
| 9 | 6i | Ph | 4-MeO—$C_6H_4$ | 12 | 100 | 76.6 |
| 10 | 6j | Ph | 2-MeO—$C_6H_4$ | 14 | 100 | 81.4 |

[a]The reaction was carried out at room temperature under an initial hydrogen pressure of 1000 psi. The catalyst was made in situ by stirring a solution of $[Ir(COD)Cl]_2$ and (R,R) f-Binaphane in $CH_2Cl_2$. [Substrate (0.1M)]:[Ir]:(R,R) f-Binaphane = 100:1:1.1.
[b]Enantiomeric excesses were determined by chiral GC with a Supelco chiral select 1000 column. Absolute configurations were not determined.

Changing the electronic property of Ar group has little effect on both reactivity and enantioselectivity (entries 3–4), but replacing the Ar with alkyl group cause a substantial drop of enantioselectivity and reactivity (entries 6–8). The high enantioselectivity %ee) and low reactivity (23.8% yield) was achieved he ketamine derived from α-tetralone (entry 5). cement of N—Ar' group with methoxyl substituted phenyl group has great improvement in reactivity without any increment of enantioselectivity (entries 9–10). This is understandable that the electron donating methoxyl group can destablize the conjugate system and activated the C=N bond. Base on above facts, the highest enantioselectivity of substrate N-2,6-dimethylphenyl ketaimine may be attributable to the steric effect rather than the electronic effect of the dimethyl group.

Two substrates (6k and 6l) have been tried under the optimal hydrogenation condition with complete conversions. The hydrogenation products were subjected to deprotection with CAN in MeOH and water at 0° C. After workup, the chiral amines were purified by chromatography on silica gel. The enantioselectivities (98.1%ee and 95.7%ee for 8k and 8l respectively) are comparable to their uncleavable analogues. The highly enantioselective hydrogenation of acyclic imines is illustrated below.

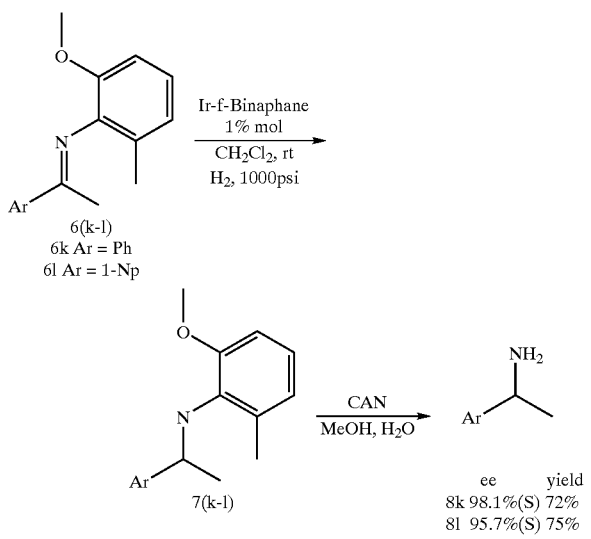

Thus, the Ir-f-binaphane complex of the present invention, having a chiral ligand with binaphthyl motif connected by a ferrocene backbone, produces the highest enantioselectivity yet achieved for asymmetric hydrogenation of acyclic imines.

The significance of the new methodology is that it provides a practical method for the synthesis of chiral primary amines.

General Procedure for the Synthesis of Imines 6(a–l)

The ketone (1 eq) and the appropriate amine (1 eq) were dissolved in dry toluene (40 ml) in a flask under nitrogen. The catalytic amount of p-toluenesulfonic acid was added. The flask was equipped with a reflux condenser and a Dean-Stark trap and the mix was heated to reflux for 5 hrs. The reaction was quenched by adding saturated $NaHCO_3$ solution and extracted with ether (3×100 ml). The organic layer was combined, washed with brines, dried ($Na_2SO_4$) and either distilled in vacuo or chromatographed on basic $Al_2O_3$.

N-(1-Phenylethylidene)aniline (6a): Schnider, P.; Koch, G.; Pretot, R.; Wang, G.; Bohnen, F.-M.; Kruger, C.; Pfaltz, A. Chem. Eur. J. 1997, 887.

N-(1-Phenylethylidene)2,6-xylxlamine(6b): Schnider, P.; Koch, G.; Pretot, R.; Wang, G.; Bohnen, F.-M.; Kruger, C.; Pfaltz, A. Chem. Eur. J. 1997, 887 and Okamoto, H.; Kato, S.; Ogasawara, M.; Konnal, M.; Takematsu, T. Agric. Biol. Chem.; EN, 55, 11, 1991, 2733.

N-(1-p-Methoxyphenylidene)2,6-xylxlamine (6c): Okamoto, H.; Kato, S.; Ogasawara, M.; Konnai, M.; Takematsu, T. Agric. Biol. Chem.; EN, 55, 11, 1991, 2733.

N-(1-p-Trifluromethylphenylidene)2,6-xylxlamine (6d): $^1$H NMR ($CDCl_3$, 300 MHz), δ8.06–8.04(2H, d, J=6.73 Hz, Ar—H), 7.64–7.62(2H, d, J=6.91 Hz, Ar—H), 6.99–6.96 (2H, d, J=6.30 Hz, Ar—H), 6.87–6.83(1H, t, Ar—H), 2.00(3H, s, $CH_3$), 1.93(6H, s, Ar$CH_3$) $^{13}$C NMR($CDCl_3$, 300 MHz), δ164.75, 148.86, 142.49, 133.16, 132.80, 132.44, 132.08, 128.96, 128.38, 127.88, 125.93, 125.87, 125.83, 125.79, 125.75, 123.61, 122.94, 119.93, 18.30, 17.91 ppm.

N-(2,3,4-Trihydro-1-naphthylidene)2,6-xylxlamine (6e): $^1$H NMR($CDCl_3$, 360 MHz) δ8.86–8.84(1H, d, J=7.69 Hz, Ar—H), 7.76–7.66(2H, m, Ar—H), 7.58–7.56(1H, d, J=7.39 Hz, Ar—H), 7.43–7.41(2H, d, J=7.45 Hz, Ar—H), 7.30–7.26(1H, t, Ar—H), 3.28–3.24(2H, t, $CH_2$), 2.64–2.60(2H, t, $CH_2$), 2.41(6H, s, $CH_3$), 2.29–2.22(2H, m, $CH_2$). $^{13}$C NMR ($CDCl_3$, 360 MHz) δ165.52, 149.61, 141.71, 134.10, 131.17, 129.32, 128.36, 128.06, 126.95, 126.18, 123.12, 30.57, 30.51, 23.36, 18.59 ppm.

N-(1-Tetrabutylethylidene)2,6-xylxlamine (6f): $^1$H NMR ($CDCl_3$, 360 MHz), δ7.22–7.20(2H, d, J=7.56 Hz, Ar—H), 7.08–7.04(1H, t, Ar—H), 2.19(3H, s, $CH_3$), 1.84(3H, s, $CH_3$), 1.50(6H, s, $CH_3$). $^{13}$C NMR ($CDCl_3$, 360 MHz) δ177.29, 149.33, 128.63, 128.28, 127.97, 125.70, 122.93, 122.65, 122.31, 40.98, 28.46, 18.06, 15.69 ppm.

N-(1-Isopropylethylidene)2,6-xylxlamine (6 g): [1]NMR ($CDCl_3$, 360 MHz) δ7.00–6.98(2H, d, J=7.52 Hz, Ar—H), 6.87–6.83(1H, t, Ar—H), 2.73–2.65(1H, m, CH), 1.99(6H, s, Ar$CH_3$), 1.59(3H, s, $CH_3$), 1.25–1.21(6H, d, J=13.60 Hz, $CH_3$, major isomer (E)), 0.99–0.97(6H, d, J=6.84 Hz, $CH_3$, minor isomer (Z)) [(E)/(Z)=14:1], $^{13}$C NMR ($CDCl_3$, 360 MHz) δ175.91, 149.10, 128.23, 126.04, 122.80, 39.22, 20.41, 18.08, 17.93 ppm.

N-(1-Cyclohexylethylidene)2,6-xylxlamine (6 h): $^1$HNMR ($CDCl_3$, 360 MHz) 66.89–6.87(2H, d, J=7.46 Hz, Ar—H), 6.76–6.72(1H, t, Ar—H), 2.27–2.25(1H, m, CH), 1.88(6H, s, Ar$CH_3$), 1.92–1.50(5H, m, $CH_2$), 1.49(3H, S, $CH_3$), 1.49–1.22(5H, m, $CH_2$). $^{13}$C NMR ($CDCl_3$, 360 MHz) δ175.37, 149.21, 127.88, 125.98, 122.73, 49.41, 30.93, 26.64, 18.60, 18.15 ppm.

N-(1-Phenylidene)4'-methoxyaniline (6i): Milart, P.; Sepiol, J. Z. Naturforsch. B. Anorg. Chem. Org. Chem. EN. 41, 3, 1986, 371.

N-(1-Phenylidene)2'-methoxyaniline (6j): Okamoto, H.; Kato, S.; Ogasawara, M.; Konnal, M.; Takematsu, T. Agric. Biol. Chem.; EN, 55, 11, 1991, 2733.

N-(1-Phenylidene)2'-methoxy-6'-methylaniline (6k): $^1$H NMR ($CDCl_3$, 360 MHz) δ8.39–8.36(2H, m, Ar—H), 7.76–7.73(3H, m Ar—H), 7.31–7.28(1H, t, Ar—H), 7.18–7.16(1H, d, J=7.57 Hz, Ar—H), 7.10–7.08(1H, d, J=8.09 Hz), 4.03(3H, s, $OCH_3$), 2.42(3H, s, $CH_3$), 2.41 (3H, s, $CH_3$). $^{13}$C NMR ($CDCL_3$, 360 MHz) δ167.18, 148.68, 139.77, 139.45, 130.81, 129.04, 128.91, 128.76, 128.52, 128.29, 127.76, 126.63, 126.30, 124.14, 123.83, 123.02, 109.46, 56.10, 18.29 ppm.

N-(1-(1-Naphthyl)ethylidene)2'-methoxy-6'-methylaniline (6l): $^1$H NMR ($CDCl_3$, 360 MHz) δ8.65–8.62(1H, d, J=8.49 Hz, Ar—H), 7.94–7.92(2H, d, J=8.04 Hz, Ar—H), 7.69–7.67(1H, d, J=8.13 Hz, Ar—H), 7.62–7.54(3H, m, Ar—H), 7.08–7.06(1H, t, Ar—H), 6.96–6.70(2H, m, Ar—H), 3.93(3H, s, $OCH_3$), 2.28(3H, s, $CH_3$), 2.24(3H, s, $CH_3$). $^{13}$C NMR($CDCl_3$, 360 MHz) δ171.60, 148.38, 140.45, 139.34, 134.39, 130.93, 129.55, 128.91, 128.75, 128.63, 127.01, 126.40, 125.46, 125.16, 124.01, 123.02, 108.49, 56.30, 23.02, 18.70, 18.40 ppm.

General Procedure for Catalytic Asymmetric Hydrogenation of Imines

The Ir-f-binaphane complex was made in situ by mixing [Ir(COD)Cl]$_2$ (6.7 mg, 0.01 mmol) and f-binaphane (17.7 mg, 0.022 mmol) in 20 mL of $CH_2Cl_2$. The mixture was stirred for 30 min. Then 5 mL of this solution was transferred to a 10 mL vial with an imine substrate (0.5 mmol). The hydrogenation was performed at rt under 1000 psi of hydrogen. After the reaction, the hydrogen was released carefully and the reaction mixture was passed through a silica gel plug eluted with $CH_2Cl_2$. The enantiomeric excess was measured by using GC with a chiral column without further purification. The absolute configuration of products was determined by comparing the retention time with the standard chiral compounds.

N-Phenyl-1-phenylethylamine (7a): Schnider, P.; Koch, G.; Pretot, R.; Wang, G.; Bohnen, F.-M.; Kruger, C.; Pfaltz, A. Chem. Eur. J. 1997, 887.

N-(2',6'-Dimethylphenyl)-1-phenylethylamine (7b): $^1$H NMR ($CDCl_3$, 360 MHz) δ7.19–7.10(5H, m, Ar—H), 6.85–6.83(2H, d, J=7.41 Hz, Ar—H), 6.70–6.66(1H, t, Ar—H), 4.24–4.19(1H, q, CH), 3.09(1H, b, NH), 2.07 (6H, s, ArCH$_3$), 1.42–1.39(3H, d, J=6.76 Hz, CH$_3$). $^{13}$C NMR($CDCl_3$, 360 MHz) δ145.75, 145.39, 129.93, 129.33, 128.91, 127.48, 126.61, 122.11, 57.27, 23.13, 19.40 ppm.

N-(2',6'-Dimethylpheny)-1-p-Methoxyphenylethylamine (7c): $^1$H NMR ($CDCl_3$, 360 MHz) δ7.35–7.33(2H, d, J=6.93 Hz, Ar—H), 7.09–7.07(2H, d, J=7.51 Hz, Ar—H), 6.98–6.90(3H, m, Ar—H), 4.44–4.39(1H, q, CH), 3.91 (3H, s, OCH$_3$), 3.30(1H, b, NH), 2.31(6H, s, ArCH$_3$), 1.63–1.61(3H, d, CH$_3$). $^{13}$C NMR ($CDCl_3$, 360 MHz), δ159.00, 145.31, 137.87, 129.91, 129.23, 127.63, 122.02, 114.06, 56.50, 55.83, 22.98, 19.35 ppm.

N-(2',6'-Dimethylphenyl)-1-p-Trifluromethylphenyl ethylamine (7d): $^1$NMR ($CDCl_3$, 300 MHz), δ7.49–7.46(2H, d, J=8.24 Hz, Ar—H), 7.35–7.32(2H, d, J=8.21 Hz, Ar—H), 6.89–6.87(2H, d, J=7.47 Hz, Ar—H), 6.75–6.70 (1H, t, Ar—H). 4.32–4.25(1H, q, CH), 3.11(1H, b, NH), 2.08(6H, s, ArCH$_3$), 1.47–1.44(3H, d, J=6.74 Hz, CH$_3$). $^{13}$C NMR ($CDCl_3$, 360 MHz), δ144.90, 129.74, 129.37, 126.87, 126.40, 125.82, 122.80, 122.35, 56.98, 23.26, 19.30 ppm.

N-(2',6'-Dimethylphenyl)-2,3,4-trihydro-1-naphthylamine (7e): The $^1$NMR spectrum was consistent with 7e.

N-(2',6'-Dimethylphenyl)-1-Tetrabutylethylamine (7f): $^1$NMR ($CDCl_3$, 360 MHz) δ6.88–6.85(2H, d, J=7.44 Hz, Ar—H), 6.69–6.65(1H, t, Ar—H), 3.08–3.02(1H, q, CH), 2.82(1H, b, NH), 2.16(6H, s, ArCH$_3$), 0.96(9H, s, CH$_3$), 0.79–0.77(3H, d, J=6.49 Hz, CH$_3$). $^{13}$C NMR ($CDCl_3$, 360 MHz) δ145.78, 129.46, 129.29, 121.31, 60.29, 35.33, 27.00, 19.73, 15.75 ppm.

N-(2',6'-Dimethylphenyl)-1-Isopropylethylamine (7g): $^1$H NMR ($CDCl_3$, 360 MHz) δ6.90–6.88(2H, d, J=7.46 Hz, Ar—H), 6.71–6.67(1H, t, ArH), 3.14–3.07(1H, m, CH), 2.90(1H, b, NH), 2.18(6H, s, ArCH$_3$), 2.14–1.66(1H, m, CH), 0.94–0.86(9H, m, CH$_3$). $^{13}$C NMR ($CDCl_3$, 360 MHz) δ145.57, 129.34, 129.07, 121.30, 57.49, 33.87, 19.91, 19.58, 17.99, 17.22 ppm.

N-(2',6'-Dimethylphenyl)-1-Cyclohexylethylamine (7h): $^1$H NMR ($CDCl_3$, 360 MHz) δ6.90–6.88(2H, d, J=7.42 Hz, Ar—H), 6.72–6.68(1H, t, Ar—H), 3.08–3.03(1H, m, CH), 2.91(1H, b, NH), 2.18(6H, s, ArCH$_3$), 1.91–1.55(5H, m, CH/CH$_2$), 1.17–1.08(6H, m, CH$_2$), 0.89–0.87(3H, d, J=6.51 Hz, CH$_3$). $^{13}$C NMR ($CDCl_3$, 360 MHz) δ129.24, 128.22, 121.36, 57.29, 44.52, 30.43, 28.80, 27.12, 27.01, 26.90, 19.57 ppm.

N-(p-Methoxyphenyl)-1-phenylethylamine (7I): $^1$H NMR ($CDCl_3$, 360 MHz) δ7.27–7.20(4H, m, Ar—H), 7.13–7.10(1H, t, Ar—H), 6.60–6.58(2H, d, J=6.69 Hz, Ar—H), 6.37–6.35(2H, d, J=6.70 Hz, Ar—H), 4.33–4.28 (1H, m, CH), 3.58(1H, b, NH), 3.57(6H, s, ArCH$_3$), 1.39–1.37(3H, d, J=6.70 Hz, CH$_3$). $^{13}$C NMR ($CDCl_3$, 360 MHz) δ152.39, 145.95, 142.00, 129.09, 127.30, 126.38, 115.23, 115.07, 56.17, 54.74, 25.57 ppm.

N-(o-Methoxyphenyl)-1-phenylethylamine (7j): $^1$H NMR ($CDCl_3$, 360 MHz) 7.28–7.26(2H, d, J=8.60 Hz, Ar—H), 7.26–7.18(2H, m, Ar—H), 7.10–7.04(1H, t, Ar—H), 6.67–6.58(2H, m, Ar—H), 6.51–6.48(1H, t, Ar—H), 6.26–6.24(1H, d, J=7.75 Hz, Ar—H), 4.57(1H, b, NH), 4.40–4.35(1H, m, CH), 3.77(3H, s, OCH$_3$), 1.46–1.44 (3H, d, J=6.76 Hz, CH$_3$). $^{13}$C NMR ($CDCl_3$, 360 MHz) δ147.05, 145.88, 137.62, 129.07, 127.26, 126.32, 121.63, 116.83, 111.56, 109.74, 55.88, 53.81, 25.62 ppm.

N-(2'-Methoxy-6'-methylphenyl)-1-phenylethylamine (7k): $^1$H NMR ($CDCl_3$, 360 MHz) δ7.22–7.14(4H, m, Ar—H), 7.09–7.07(1H, t, Ar—H), 6.69–6.64(1H, t, Ar—H), 6.59–6.53(2H, m, Ar—H), 4.44–4.39(m, 1H, CH), 3.83 (1H, b, NH), 3.63(3H, s, OCH$_3$), 2.16(3H, s, ArCH$_3$), 1.39–1.37(3H, d, J=6.73 Hz, CH$_3$). $^{13}$C NMR ($CDCl_3$, 360 MHz) δ151.77, 146.14, 136.24, 129.81, 128.63, 127.31, 126.59, 124.01, 121.44, 108.98, 56.67, 56.13, 23.90, 19.33 ppm.

N-(2'-Methoxy-6'-methylphenyl)-1-naphthylethylamine (7l): $^1$H NMR ($CDCl_3$, 300 MHz) 68.08–8.05(1H, d, J=8.06 Hz, Ar—H), 7.74–7.71(1H, d, J=7.49 Hz, Ar—H), 7.61–7.59(1H, D, J=8.16 Hz, Ar—H), 7.54–7.51(1H, d, J=6.84 Hz, Ar—H), 7.38–7.30(3H:, m, Ar—H), 6.64–6.54(3H, m, Ar—H), 5.39–5.33(1H, m, CH), 4.08 (1H, b, NH), 3.64(3H, s, OCH$_3$), 2.13(3H, s, ArCH$_3$), 1.48–1.46(3H, d, J=6.66 Hz, CH$_3$). $^{13}$C NMR($CDCl_3$, 300 MHz) δ151.25, 142.46, 136.52, 134.32, 131.42, 129.29, 128.92, 127.62, 126.30, 126.04, 125.76, 124.23, 123.62, 122.86, 120.87, 109.09, 56.17, 52.37, 24.32, 19.61 ppm.

General Procedure for Deprotection of Amines 7(k–l)

The N-protected amine 7k/7l was dissolved in a mixture of MeOH/H$_2$O (4:1). CAN (4eq) was added at 0° C., and the mixture was stirred for 6 h at the same temperature. Water was added and the solution was washed with $CH_2Cl_2$. The aqueous solution was made alkaline by adding 1N NaOH, and then extracted with ethyl acetate. The combined organic layer was washed with brine and dried over Na$_2$SO$_4$. The solvent was removed and the residue was subject to chromatography to afford the pure product 8k/8l.

Another potential application of this transformation is the synthesis of chiral agrochemicals. The preparation of (R)-metalaxyl and (S)-metolachor is shown below.

Synthesis of Agrochemicals via Imine Reduction

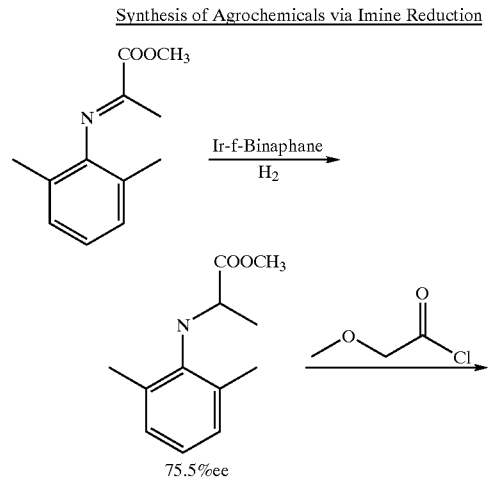

75.5%ee

-continued

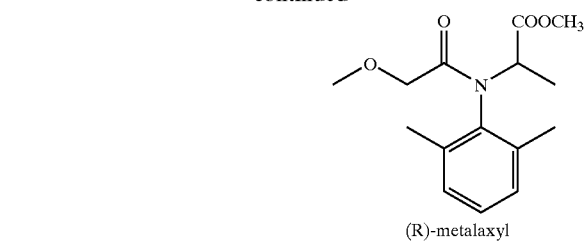

(R)-metalaxyl

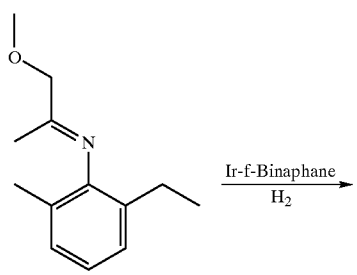

↓ Ir-f-Binaphane
  H₂

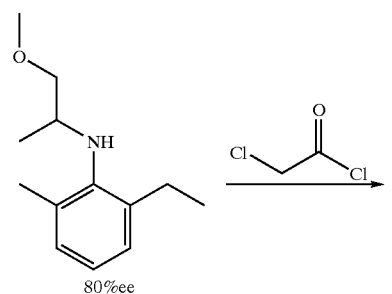

80%ee

↓ + ClCOCH₂Cl (chloroacetyl chloride)

(s)-metolachor

Alternative work-up and isolation procedures are also possible, and will be evident to those skilled in the art.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A chiral ligand selected from the group consisting of compounds represented by A and its enantiomer:

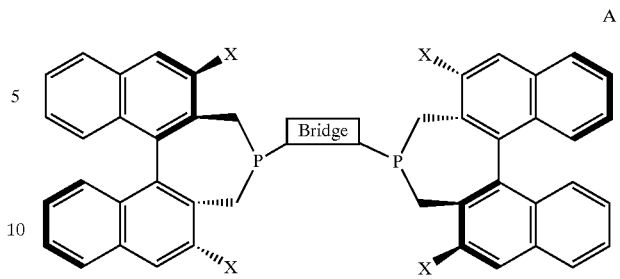

A wherein the bridge group is selected from the group consisting of: $(CH_2)_n W(CH_2)_m$ wherein n and m are independently an integer ranging from 1 to 8 and W, wherein W is a divalent group selected from the group consisting of: ferrocene, and a substituted derivative thereof; wherein each substituent in said substituted derivative is selected from the group consisting of: aryl, alkyl having 1–8 carbon atoms, F, Cl, Br, I, COOR, $SO_3R$, $PR_3R_2$, OR, SR, $PR_2$, $AsR_2$, $SbR_2$, aryloxyl, nitro, $NR_2$, vinyl, substituted vinyl and a combination thereof, wherein each R is independently selected from the group consisting of: hydrogen, alkyl, aryl, alkaryl and aralkyl; wherein each X is independently selected from the group consisting of: hydrogen, halide, alkyl, aryl, alkoxy, silane, carboxylate and amide.

2. A chiral ligand having an optical purity of at least 85%ee, selected from the group consisting of compounds represented by A and its enantiomer:

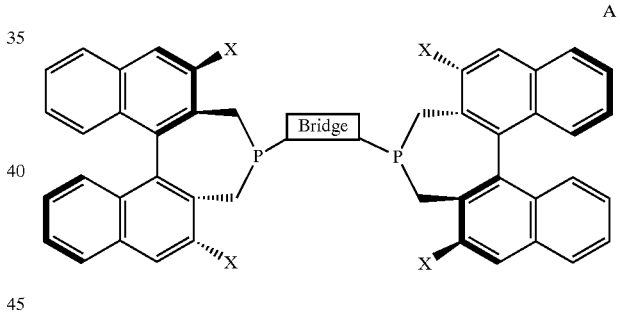

A wherein the bridge group is selected from the group consisting of: $(CH_2)_n$ wherein n is an integer ranging from 1 to 8, $(CH_2)_n W(CH_2)_m$ wherein n and m are independently an integer ranging from 1 to 8 and W, wherein W is a divalent group selected from the group consisting of: 1,2-divalent phenyl, 2,2'-divalent 1,1'-biphenyl, 2,2'-divalent-1,1'-binaphthyl, ferrocene, and a substituted derivative thereof; wherein each substituent in said substituted derivative is selected from the group consisting of: aryl, alkyl having 1–8 carbon atoms, F, Cl, Br, I, COOR, $SO_3R$, $PR_3R_2$, OR, SR, $PR_2$, $AsR_2$, $SbR_2$, aryloxyl, nitro, $NR_2$, vinyl, substituted vinyl and a combination thereof, wherein each R is independently selected from the group consisting of: hydrogen, alkyl, aryl, alkaryl and aralkyl; wherein each X is independently selected from the group consisting of: hydrogen, halide, alkyl, aryl, alkoxy, silane, carboxylate and amide.

3. The ligand of claim 2, having an optical purity of at least 95%ee.

4. The ligand of claim 2, selected from the group consisting of L1, L2, L4–L8 and enantiomers thereof:

L1
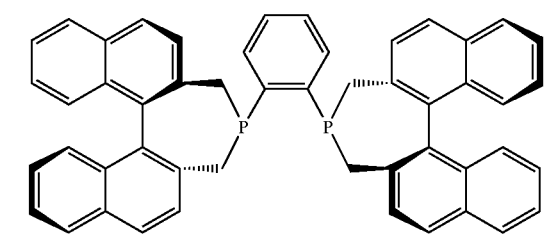

L2
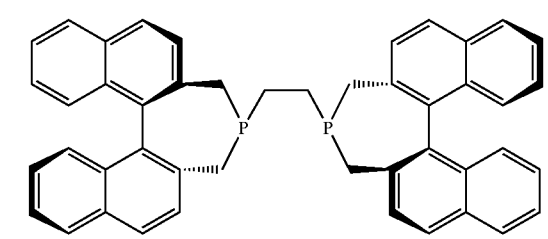

L4
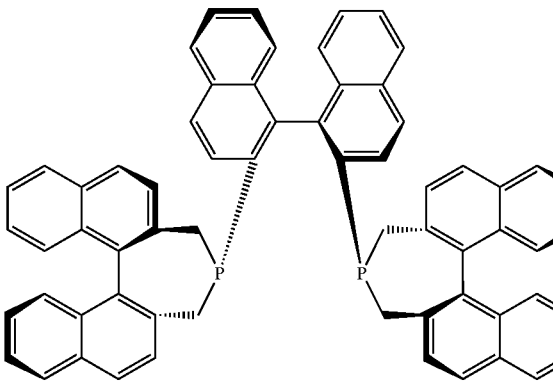

L5
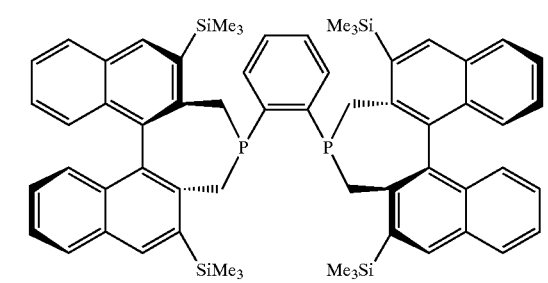

L6
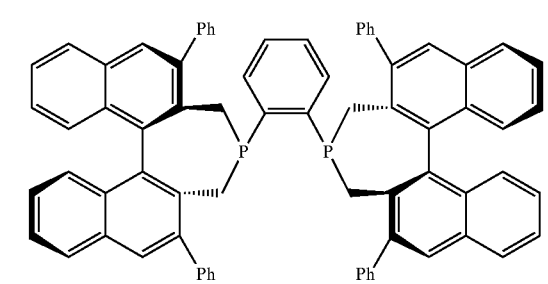

L7
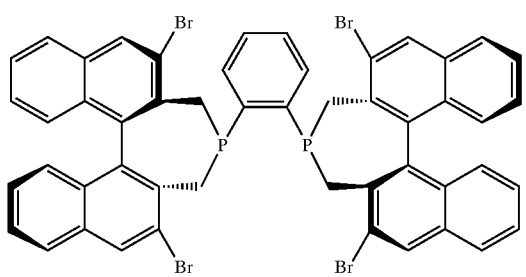

L8
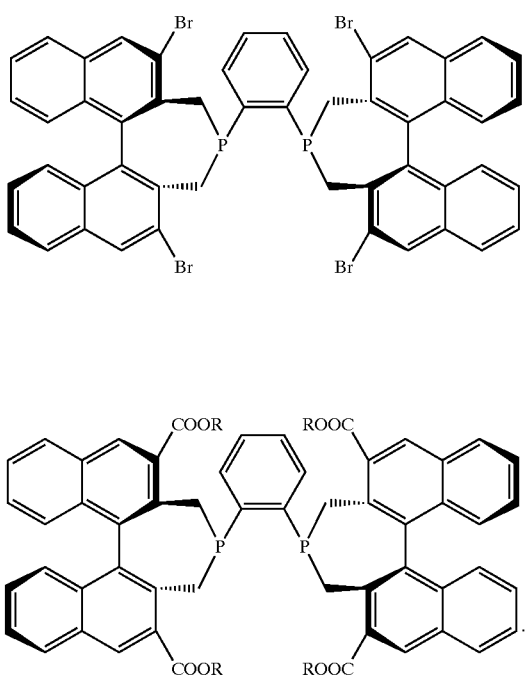

5. A chiral f-binaphane ligand selected from the group consisting of compounds represented by the formula A or enantiomers thereof:

A
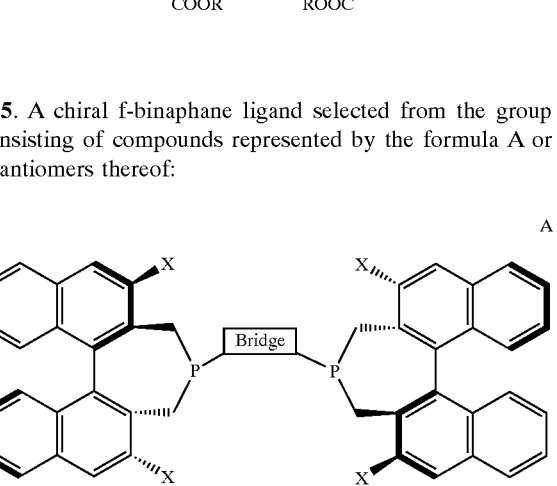

wherein the bridge group is selected from the group consisting of: $(CH_2)_nW(CH_2)_m$ wherein n and m are independently an integer ranging from 1 to 8 and W, wherein W is ferrocene or a substituted derivative thereof; wherein each substituent in said substituted derivative is selected from the group consisting of: aryl, alkyl having 1–8 carbon atoms, F, Cl, Br, I, COOR, $SO_3R$, $PR_3R_2$, OR, SR, $PR_2$, $AsR_2$, $SbR_2$, aryloxyl, nitro, $NR_2$, vinyl, substituted vinyl and a combination thereof, wherein each R is independently selected from the group consisting of: hydrogen, alkyl, aryl, alkaryl and aralkyl; and wherein each X is independently selected from the group consisting of: hydrogen, halide, alkyl, aryl, alkoxy, silane, carboxylate and amide.

6. The ligand of claim 5, wherein said ligand is (R,R)-f-binaphane represented by the formula:

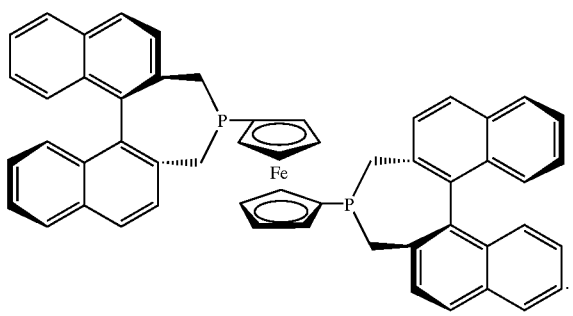

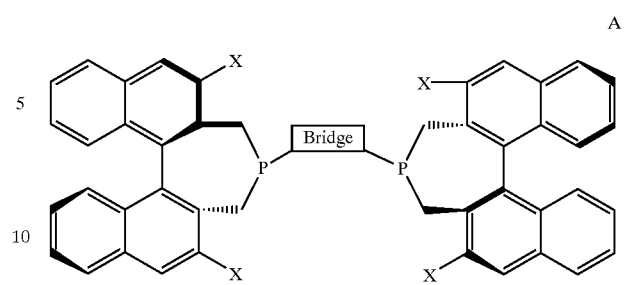

7. A ligand selected from the group consisting of: L3, L16, L24 and their enantiomers, wherein L3, L16 and L24 are represented, respectively, by the following formulas:

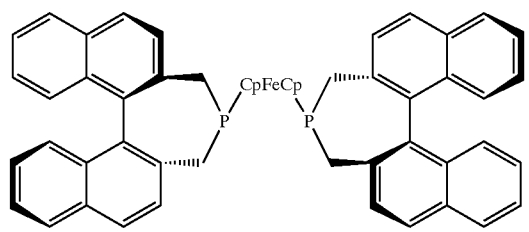

L3

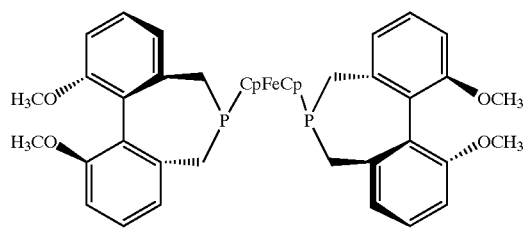

L16

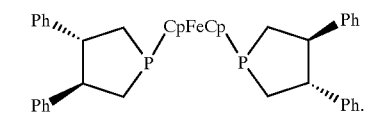

L24

8. The ligand of claim 7, wherein said ligand is a racemic mixture of enantiomers.

9. The ligand of claim 7, wherein said ligand is a non-racemic mixture of enantiomers.

10. The ligand of claim 7, having an optical purity of at least 85%ee.

11. The ligand of claim 7, having an optical purity of at least 95%ee.

12. A ligand selected from the group consisting of compounds represented by A and its enantiomer:

wherein the bridge group is selected from the group consisting of: $(CH_2)_n$ wherein n is an integer ranging from 1 to 8, $(CH_2)_n W(CH_2)_m$ wherein n and m are independently an integer ranging from 1 to 8 and W, wherein W is a divalent group selected from the group consisting of: 1,2-divalent phenyl, 2,2'-divalent 1,1'-biphenyl, 2,2'-divalent-1,1'-binaphthyl and a substituted derivative thereof; wherein each substituent in said substituted derivative is selected from the group consisting of: aryl, alkyl having 1–8 carbon atoms, F, Cl, Br, I, COOR, $SO_3R$, $PR_3R_2$, OR, SR, $PR_2$, $AsR_2$, $SbR_2$, aryloxyl, nitro, $NR_2$, vinyl, substituted vinyl and a combination thereof, wherein each R is independently selected from the group consisting of: hydrogen, alkyl, aryl, alkaryl and aralkyl; wherein each X is independently selected from the group consisting of: halide, alkyl, aryl, alkoxy, silane, carboxylate and amide.

13. The ligand of claim 12, wherein said ligand is a non-racemic mixture of enantiomers.

14. The ligand of claim 12, wherein said ligand is selected from the group consisting of: L5, L6, L7, L8 and their enantiomers, wherein L5, L6, L7 and L8 are represented, respectively, by the following formulas:

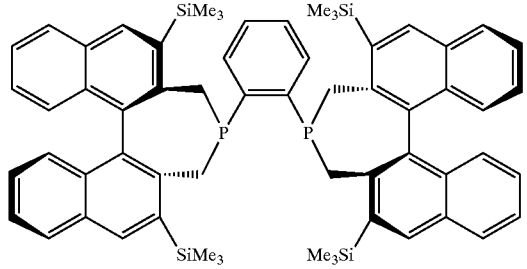

L5

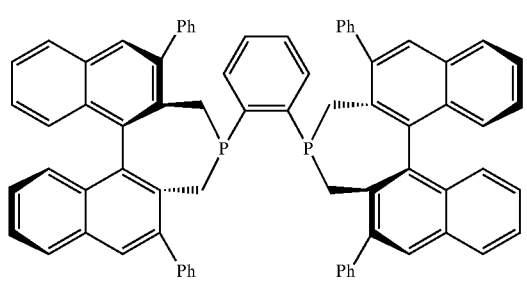

L6

L7

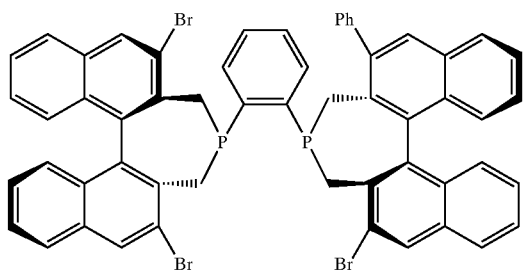

L8

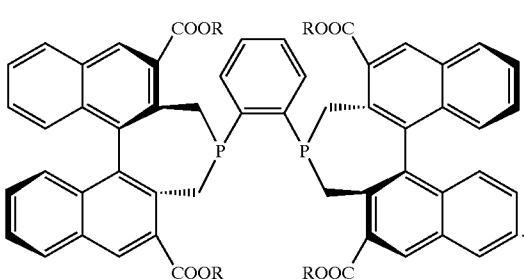

15. A ligand selected from the group consisting of compounds represented by B and its enantiomer:

B

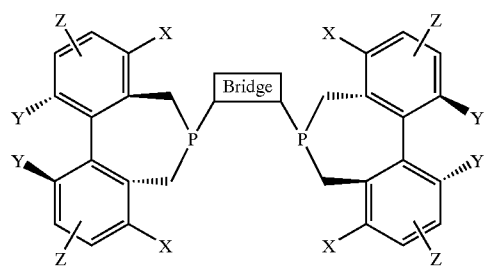

wherein the bridge group is selected from the group consisting of: $(CH_2)_n$ wherein n is an integer ranging from 1 to 8, $(CH_2)_nW(CH_2)_m$ wherein n and m are independently an integer ranging from 1 to 8 and W, wherein W is a divalent group selected from the group consisting of: 1,2-divalent phenyl, 2,2'-divalent 1,1'-biphenyl, 2,2'-divalent-1,1'-binaphthyl and a substituted derivative thereof; wherein each substituent in said substituted derivative is selected from the group consisting of: aryl, alkyl having 1–8 carbon atoms, F, Cl, Br, I, COOR, $SO_3R$, $PR_3R_2$, OR, SR, $PR_2$, $AsR_2$, $SbR_2$, aryloxyl, nitro, $NR_2$, vinyl, substituted vinyl and a combination thereof, wherein each R is independently selected from the group consisting of: hydrogen, alkyl, aryl, alkaryl and aralkyl; wherein each X is independently selected from the group consisting of: halide, alkyl, aryl, alkoxy, silane, carboxylate and amide; each Y is independently selected from the group consisting of: hydrogen, alkyl, aryl, alkoxy, carboxylate and amide; and each Z is independently selected from the group consisting of: hydrogen, alkyl, aryl, alkoxy, amide and carboxylate.

16. The ligand of claim 15, wherein said ligand is a non-racemic mixture of enantiomers.

17. The ligand of claim 16, wherein said ligand is selected from the group consisting of: L9, L10, L11, L12, L13, L14, L15, and their enantiomers, wherein L9, L10, L11, L12, L13, L14 and L15 are represented, respectively, by the following formulas:

L9

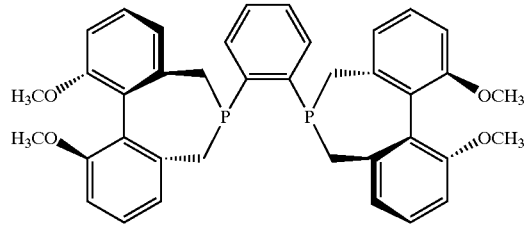

L10

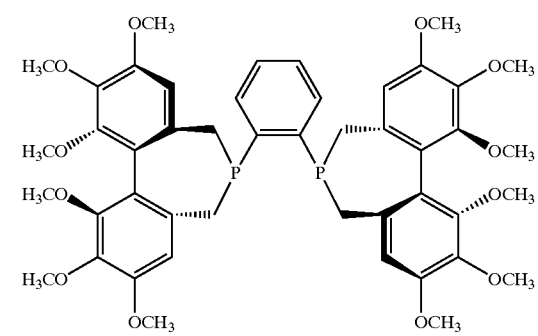

L11

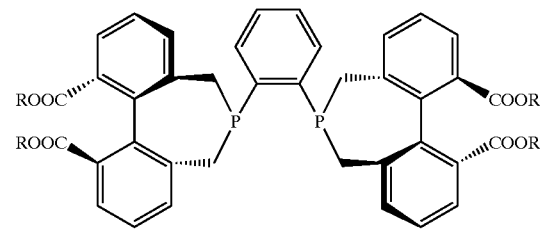

L12

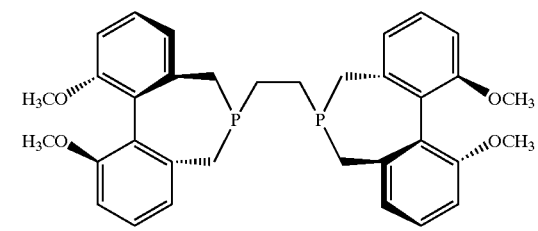

L13

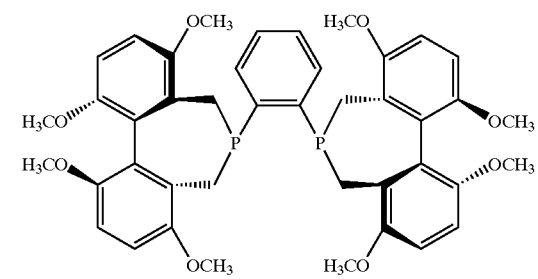

L14

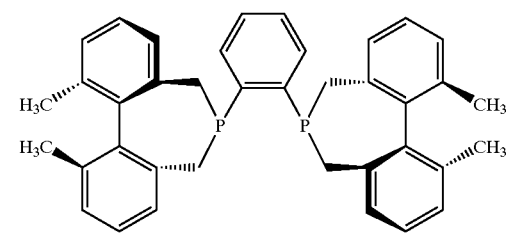

-continued

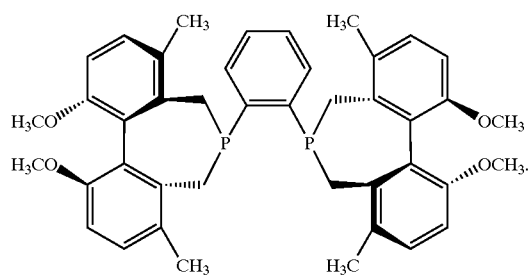
L15

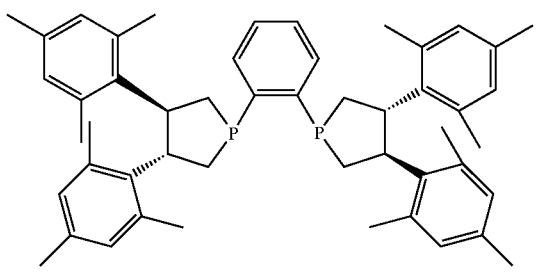
L18

18. A ligand selected from the group consisting of compounds represented by C and its enantiomer:

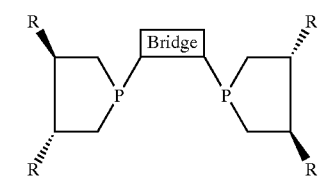
C wherein the bridge group is selected from the group consisting of: $(CH_2)_n$ wherein n is an integer ranging from 1 to 8, $(CH_2)_nW(CH_2)_m$ wherein n and m are independently an integer ranging from 1 to 8 and W, wherein W is a divalent group selected from the group consisting of: 1,2-divalent phenyl, 2,2'-divalent 1,1'-biphenyl, 2,2'-divalent-1,1'-binaphthyl and a substituted derivative thereof; wherein each substituent in said substituted derivative is selected from the group consisting of: aryl, alkyl having 1–8 carbon atoms, F, Cl, Br, I, COOR, $SO_3R$, $PR_3R_2$, OR, SR, $PR_2$, $AsR_2$, $SbR_2$, aryloxyl, nitro, $NR_2$, vinyl, substituted vinyl and a combination thereof, wherein each R is independently selected from the group consisting of: alkyl, aryl, alkaryl and aralkyl.

19. The ligand of claim 18, wherein said ligand is a non-racemic mixture of enantiomers.

20. The ligand of claim 17, wherein said ligand is selected from the group consisting of: L17, L18, L19, L20, L21, L22, L23 and their enantiomers, wherein L17, L18, L19, L20, L21, L22 and L23 are represented, respectively, by the following formulas:

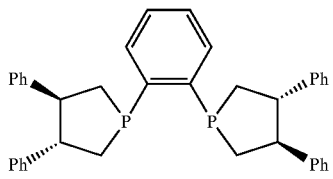
L17

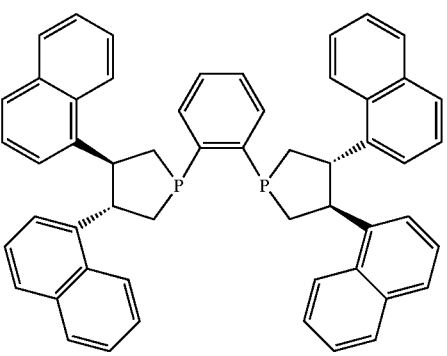
L19

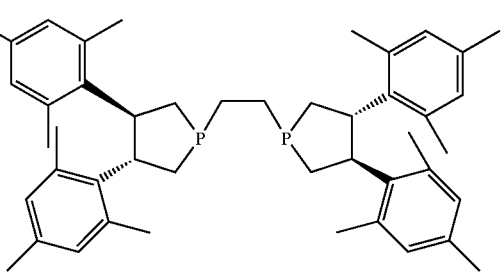
L20

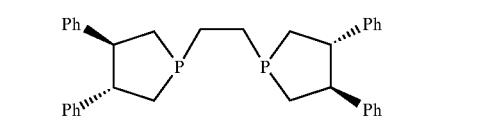
L21

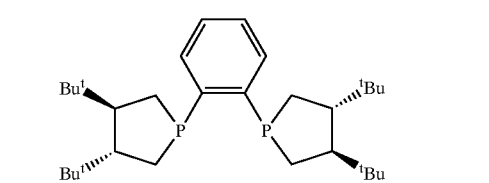
L22

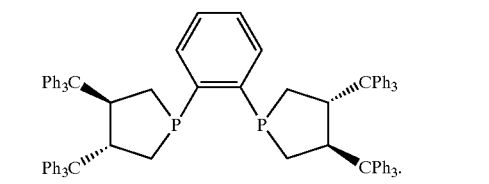
L23

21. The ligand of claim 5, wherein said ligand is (S,S)-f-binaphane.

* * * * *

UNITED STATES PATENT AND TRADEMARK OFFICE
CERTIFICATE OF CORRECTION

PATENT NO. : 6,525,210 B1
DATED : February 25, 2003
INVENTOR(S) : Xumu Zhang and Dengming Xiao It is certified that error appears in the above-identified patent and that said Letters Patent is hereby corrected as shown below:

<u>Column 1,</u>
Line 9, please insert the following:
-- STATEMENT OF GOVERNMENT RIGHTS
　　This invention was made with support from the Government under Grant No. 1R01 GM58832. The Government has certain rights in the invention. --.

Signed and Sealed this

Fifteenth Day of November, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,525,210 B1 | Page 1 of 1 |
| APPLICATION NO. | : 09/643434 | |
| DATED | : February 25, 2003 | |
| INVENTOR(S) | : Zhang et al. | |

It is certified that error appears in the above-identified patent and that said Letters Patent is hereby corrected as shown below:

In the Description
Column 1,
Line 9, after "...Nov. 15, 1999." please insert the following Heading and paragraph:

--STATEMENT OF GOVERNMENT RIGHTS
This invention was made with Government support under Grant No. 1R01 GM58832, awarded by the National Institutes of Health and Contract No. N00014-96-1-0733, awarded by the Office of Naval Research. The Government has certain rights in the invention.--

Signed and Sealed this

Eighth Day of July, 2008

JON W. DUDAS
*Director of the United States Patent and Trademark Office*